US011479957B2

(12) United States Patent
Schwab et al.

(10) Patent No.: US 11,479,957 B2
(45) Date of Patent: Oct. 25, 2022

(54) MEDICINE DELIVERY, WASH, CLEAN AND AIR DRY SYSTEM

(71) Applicant: Bemis Manufacturing Company, Sheboygan Falls, WI (US)

(72) Inventors: Brian Schwab, East Chatham, NY (US); Shao-Yu Peng, Changhua County (TW)

(73) Assignee: Bemis Manufacturing Company, Sheboygan Falls, WI (US)

( * ) Notice: Subject to any disclaimer, the term of this patent is extended or adjusted under 35 U.S.C. 154(b) by 0 days.

(21) Appl. No.: 15/588,640

(22) Filed: May 6, 2017

(65) Prior Publication Data

US 2017/0321408 A1    Nov. 9, 2017

Related U.S. Application Data

(60) Provisional application No. 62/333,152, filed on May 6, 2016.

(51) Int. Cl.
*E03D 9/08*        (2006.01)
*B05B 15/70*       (2018.01)
(Continued)

(52) U.S. Cl.
CPC ............... *E03D 9/08* (2013.01); *A47K 10/48* (2013.01); *A47K 13/24* (2013.01); *A61M 3/022* (2014.02); *A61M 3/0279* (2013.01); *A61M 3/06* (2013.01); *B05B 1/005* (2013.01); *B05B 15/656* (2018.02); *B05B 15/70* (2018.02); *A61M 3/0233* (2013.01); *A61M 2205/3379* (2013.01); *A61M 2205/3561* (2013.01); *A61M 2205/505* (2013.01)

(58) Field of Classification Search
CPC ................................... E03D 9/08; A61M 3/06
USPC ...................... 4/420.1, 420.2, 420.4, 420.5
See application file for complete search history.

(56) References Cited

U.S. PATENT DOCUMENTS

| 2,875,450 | A | 3/1959 | Umann |
|---|---|---|---|
| D198,085 | S | 4/1964 | Rich |

(Continued)

FOREIGN PATENT DOCUMENTS

| DE | 1625201 | 2/1970 |
|---|---|---|
| EM | 025022450001 | 7/2014 |

(Continued)

OTHER PUBLICATIONS

Machine Translation of JP2014163153A. Espacenet. (Year: 2021).*
(Continued)

*Primary Examiner* — Christine J Skubinna
(74) *Attorney, Agent, or Firm* — Michael Best & Friedrich LLP

(57) ABSTRACT

The present disclosure provides a toilet seat assembly for delivering medicine, washing, cleaning, and drying a perineal region of a user. The toilet seat assembly includes a spraying nozzle assembly having one or more retractable spray nozzle units for delivering a liquid product, a drying nozzle assembly having one or more retractable drying nozzle units for drying the region, and a medicine delivery assembly for delivering a medicinal product to the region, the medicine delivery assembly having a medicine delivery nozzle connected to a medicine storage element containing the medicinal product.

15 Claims, 16 Drawing Sheets

(51) Int. Cl.
  *B05B 1/00*    (2006.01)
  *A61M 3/02*    (2006.01)
  *B05B 15/656*  (2018.01)
  *A47K 10/48*   (2006.01)
  *A47K 13/24*   (2006.01)
  *A61M 3/06*    (2006.01)

(56) References Cited

U.S. PATENT DOCUMENTS

| | | |
|---|---|---|
| 3,306,252 A | 2/1967 | Knight |
| 3,516,424 A | 6/1970 | Eagle |
| 3,810,260 A | 5/1974 | Lodi |
| 3,995,326 A | 12/1976 | Umann |
| 4,067,499 A | 1/1978 | Cohen |
| 4,279,362 A | 7/1981 | Pursell |
| 4,287,618 A * | 9/1981 | Silver ............... E03D 9/085 4/420.2 |
| 4,327,560 A | 5/1982 | Leon et al. |
| D266,758 S | 11/1982 | Johannsen |
| 4,422,189 A | 12/1983 | Couvrette |
| 4,428,512 A | 1/1984 | Nosek |
| D279,184 S | 6/1985 | Sakamoto |
| 4,628,548 A | 12/1986 | Kurosawa et al. |
| D303,966 S | 10/1989 | Fritzsche |
| 4,903,347 A | 2/1990 | Garcia et al. |
| 4,987,617 A | 1/1991 | Furukawa et al. |
| 5,031,252 A | 7/1991 | Oyama |
| 5,101,520 A | 4/1992 | Lockhart |
| 5,201,080 A * | 4/1993 | Tanaka ............... E03D 9/08 4/443 |
| 5,203,037 A | 4/1993 | Kang |
| 5,247,711 A | 9/1993 | Kwon |
| 5,335,855 A | 8/1994 | Borod |
| D355,246 S | 2/1995 | Kawamura |
| 5,409,167 A | 4/1995 | Borod |
| D367,922 S | 3/1996 | Kobayashi |
| 5,504,948 A | 4/1996 | Chandler |
| 5,551,098 A | 9/1996 | Wilk |
| 5,566,402 A | 10/1996 | Agha el.Rifai et al. |
| 5,630,234 A | 5/1997 | Childs |
| D387,851 S | 12/1997 | Pieters |
| 5,720,054 A | 2/1998 | Makayama et al. |
| 5,765,238 A | 6/1998 | Furukawa et al. |
| 5,813,060 A | 9/1998 | Klopocinski |
| 5,864,894 A * | 2/1999 | Fedele ............... E03D 9/08 4/213 |
| 5,898,956 A | 5/1999 | Kurisaki et al. |
| 5,911,516 A | 6/1999 | Chang |
| 5,941,419 A | 8/1999 | Molinary |
| 5,953,765 A | 9/1999 | Hayashi et al. |
| 5,987,659 A | 11/1999 | Cannizzaro |
| 6,003,159 A | 12/1999 | Sadegh et al. |
| 6,009,570 A | 1/2000 | Hargest |
| D423,655 S | 4/2000 | Otte |
| 6,073,275 A | 6/2000 | Klopocinski |
| 6,105,178 A | 8/2000 | Kurisaki et al. |
| D432,220 S | 10/2000 | Hulsebus |
| 6,128,788 A | 10/2000 | Yamazaki |
| D435,638 S | 12/2000 | Merry |
| 6,167,577 B1 | 1/2001 | Hammad |
| 6,178,568 B1 | 1/2001 | Boulieris |
| 6,192,527 B1 | 2/2001 | Paul |
| D451,076 S | 11/2001 | Sommer et al. |
| D451,177 S | 11/2001 | Scholpp |
| 6,339,852 B1 | 1/2002 | Huang |
| 6,397,406 B1 | 6/2002 | Moshkovich |
| 6,449,780 B1 | 9/2002 | Merry |
| 6,481,590 B1 | 11/2002 | Simkins |
| D471,966 S | 3/2003 | Takahashi |
| D481,016 S | 10/2003 | Hillis |
| D485,337 S | 1/2004 | Tani |
| 6,688,500 B1 | 2/2004 | Cheng |
| 6,691,328 B2 | 2/2004 | Delfino |
| 6,754,912 B1 | 6/2004 | Hayashi et al. |
| D500,130 S | 12/2004 | Jung |
| D508,733 S | 8/2005 | Peng |
| D512,425 S | 12/2005 | Nakagawa |
| 6,973,679 B1 | 12/2005 | Schad |
| 7,096,518 B2 * | 8/2006 | Takenaga ............ E03D 9/08 4/420.2 |
| D528,991 S | 9/2006 | Katsuyama et al. |
| 7,120,946 B1 | 10/2006 | Lazar |
| 7,127,750 B2 | 10/2006 | Lim |
| D533,788 S | 12/2006 | Kleiman |
| 7,155,755 B2 | 1/2007 | Olivier |
| D538,907 S | 3/2007 | Kaule |
| 7,191,473 B2 | 3/2007 | Matsomoto et al. |
| D541,225 S | 4/2007 | Katsuyama et al. |
| 7,216,374 B2 | 5/2007 | Hassan |
| 7,284,285 B2 | 10/2007 | Scalzi |
| 7,287,286 B2 | 10/2007 | Lee |
| D554,613 S | 11/2007 | Nakatani |
| D558,181 S | 12/2007 | Takada |
| D564,976 S | 3/2008 | Billings et al. |
| D565,554 S | 4/2008 | Fan |
| D578,515 S | 10/2008 | Ikeda et al. |
| D579,342 S | 10/2008 | Priestman |
| D583,030 S | 12/2008 | Kobayashi |
| D594,537 S | 6/2009 | Driedger |
| D594,945 S | 6/2009 | Nakasaki et al. |
| 7,543,339 B1 | 6/2009 | Harris |
| D608,426 S | 1/2010 | Watanabe |
| D616,445 S | 5/2010 | Wong et al. |
| D634,735 S | 3/2011 | Maier |
| D639,399 S | 6/2011 | Takeuchi |
| D639,400 S | 6/2011 | Kang |
| 7,954,181 B2 | 6/2011 | Lim |
| 8,060,953 B1 | 11/2011 | Dorra |
| D654,808 S | 2/2012 | Gidlow |
| 8,161,580 B2 | 4/2012 | Hashidume et al. |
| 8,261,377 B2 | 9/2012 | Oh |
| D668,642 S | 10/2012 | Feldman et al. |
| 8,291,527 B2 | 10/2012 | Pan et al. |
| D670,659 S | 11/2012 | Ishikawa et al. |
| D671,935 S | 12/2012 | Mao |
| 8,365,317 B1 | 2/2013 | Dorra |
| 8,425,475 B2 | 4/2013 | Sodo |
| D682,246 S | 5/2013 | Boqueho |
| D688,359 S | 8/2013 | Ogata et al. |
| D692,417 S | 10/2013 | Tu |
| D692,541 S | 10/2013 | Hosoi et al. |
| D698,754 S | 2/2014 | Vignau-Lous |
| D703,797 S | 4/2014 | Shinozaki |
| D704,316 S | 5/2014 | Yoshioka |
| D704,317 S | 5/2014 | Ando |
| D706,402 S | 6/2014 | Yeung |
| D708,954 S | 7/2014 | Barnes |
| 8,776,278 B1 | 7/2014 | Dorra |
| D713,815 S | 9/2014 | Ookawa |
| D715,774 S | 10/2014 | Lee et al. |
| D716,768 S | 11/2014 | Kim |
| D717,930 S | 11/2014 | Kergoet |
| 8,904,575 B1 | 12/2014 | Lindheimer et al. |
| D724,058 S | 3/2015 | Chandel |
| D724,059 S | 3/2015 | Kim |
| 9,049,970 B2 | 6/2015 | Dorra |
| 9,084,864 B1 | 7/2015 | Schroeder et al. |
| D750,765 S | 3/2016 | Giametta |
| 9,273,454 B2 | 3/2016 | Slawinski |
| 9,279,241 B2 | 3/2016 | Morioka et al. |
| D753,095 S | 4/2016 | Moran |
| 9,464,425 B2 | 10/2016 | Bailey |
| D781,808 S | 3/2017 | Pista |
| D792,867 S | 7/2017 | Murphy |
| D805,615 S | 12/2017 | Peng |
| 9,889,982 B2 | 2/2018 | Falcon |
| 2003/0140407 A1 | 7/2003 | Matsumoto et al. |
| 2004/0055080 A1 | 3/2004 | Marshall |
| 2005/0000006 A1 | 1/2005 | Takenaga |
| 2005/0010997 A1 | 1/2005 | Olivier |
| 2006/0000012 A1 | 1/2006 | Schad |
| 2006/0265801 A1 | 11/2006 | Riccobon |
| 2007/0241929 A1 | 10/2007 | Marchetto |

(56) References Cited

U.S. PATENT DOCUMENTS

| | | |
|---|---|---|
| 2008/0047055 A1 | 2/2008 | Lim |
| 2008/0055394 A1 | 3/2008 | Shiue |
| 2008/0201837 A1 | 8/2008 | Oh |
| 2008/0251551 A1 | 10/2008 | Huber |
| 2009/0313752 A1 | 12/2009 | Kunimoto et al. |
| 2010/0012685 A1 | 1/2010 | Ramsey |
| 2010/0152475 A1 | 6/2010 | Raichle |
| 2010/0176224 A1 | 7/2010 | Hasselschwert |
| 2011/0132929 A1 | 6/2011 | Bennett |
| 2011/0133001 A1 | 6/2011 | Cooper |
| 2011/0191950 A1 | 8/2011 | Liu |
| 2011/0203044 A1* | 8/2011 | Lim .................. E03D 9/08 |
| | | 4/447 |
| 2011/0284601 A1 | 11/2011 | Pullin |
| 2012/0005817 A1 | 1/2012 | Jeong |
| 2012/0011647 A1 | 1/2012 | Mochita |
| 2012/0150148 A1 | 6/2012 | Shi |
| 2012/0180785 A1 | 7/2012 | Trill |
| 2012/0218106 A1 | 8/2012 | Zaima et al. |
| 2012/0266483 A1 | 10/2012 | Palermo et al. |
| 2013/0133131 A1 | 5/2013 | Peng |
| 2013/0180041 A1 | 7/2013 | Ding |
| 2013/0267890 A1 | 10/2013 | Li |
| 2014/0042195 A1 | 2/2014 | Geis |
| 2014/0047626 A1 | 2/2014 | Dorra |
| 2014/0068862 A1 | 3/2014 | Al-Jafar |
| 2014/0101838 A1 | 4/2014 | Gupta et al. |
| 2014/0107409 A1 | 4/2014 | Bailey et al. |
| 2015/0000025 A1 | 1/2015 | Clements |
| 2015/0059076 A1 | 3/2015 | Tiagai |
| 2015/0203279 A1 | 7/2015 | Falcon |
| 2015/0225167 A1 | 8/2015 | Andersen |
| 2015/0337525 A1 | 11/2015 | Bailey |
| 2016/0316978 A1 | 11/2016 | Peng |
| 2017/0021116 A1 | 1/2017 | Rahmel |
| 2017/0142306 A1 | 5/2017 | Peng |
| 2017/0265624 A1 | 9/2017 | Wilson |
| 2017/0319794 A1 | 11/2017 | Schwab |
| 2017/0321406 A1 | 11/2017 | Schwab |
| 2017/0321407 A1 | 11/2017 | Schwab |
| 2018/0015238 A1 | 1/2018 | Schwab |
| 2018/0028797 A1 | 2/2018 | Schwab |
| 2018/0036473 A1 | 2/2018 | Schwab |
| 2018/0044903 A1 | 2/2018 | Schwab |

FOREIGN PATENT DOCUMENTS

| | | | | |
|---|---|---|---|---|
| EP | 2138640 | | 12/2009 | |
| EP | 2138640 A1 | | 12/2009 | |
| EP | 2742189 B1 | | 10/2016 | |
| FR | 2671294 | | 7/1992 | |
| FR | 2869596 | | 11/2005 | |
| FR | WO 2008/024005 A2 | | 2/2008 | |
| GB | 2351779 | | 1/2001 | |
| IN | 2689190001 | | 10/2015 | |
| JP | S4815806 | | 2/1973 | |
| JP | H0893034 | | 4/1996 | |
| JP | H0988165 | | 3/1997 | |
| JP | H1163666 | | 3/1999 | |
| JP | 2001279778 | | 10/2001 | |
| JP | 2003286738 | | 10/2003 | |
| JP | 2003342993 | | 12/2003 | |
| JP | 2007321443 | | 12/2007 | |
| JP | 2014163153 A | * | 9/2014 | ............... E03D 9/08 |
| KR | WO 2012/044086 A2 | | 4/2017 | |
| TW | 469317 | | 12/2001 | |
| WO | 2013020240 | | 2/2013 | |

OTHER PUBLICATIONS

PCT Notification of Transmittal of The International Search Report and The Written Opinion of The International Searching Authority, or Declaration; PCT/US2017/031485, filed on May 6, 2017 by Whole Bath, LLC.

PCT Notification of Transmittal of The International Search Report and The Written Opinion of The International Searching Authority, or Declaration, PCT/US2017/031482, filed on May 6, 2017 by Whole Bath, LLC.

PCT Notification of Transmittal of The International Search Report and The Written Opinion of The International Searching Authority, or Declaration, PCT/US2017/031483, filed on May 6, 2017 by Whole Bath, LLC.

PCT Notification of Transmittal of The International Search Report and The Written Opinion of The International Searching Authority, or Declaration; PCT/US2017/031484, filed on May 6, 2017 by Whole Bath, LLC.

U.S. Appl. No. 15/847,594, filed Dec. 19, 2019, Brian Schwab.

Final Office Action for U.S. Appl. No. 15/588,640 dated Dec. 3, 2018.

PCT Notification of Transmittal of The International Search Report and The Written Opinion of the International Searching Authority, PCT/2017/031484, dated Aug. 14, 2017.

PCT Notification of Transmittal of The International Search Report and The Written Opinion of The International Searching Authority, PCT/US2016/45932, dated Oct. 24, 2016.

PCT Notification of Transmittal of The International Search Report and The Written Opinion of The International Searching Authority, PCT/US2017/042288, dated Sep. 28, 2017.

PCT Notification of Transmittal of The International Search Report and The Written Opinion of The International Searching Authority, PCT/US2017/42253, dated Nov. 21, 2017.

Schwabcare website 2017, http://schwabcare.com/, site visited Jan. 21, 18.

Kohler, Self-Cleaning Wand, https://www.youtube.com/watch?v=z629hpdnWj8, published Oct. 12, 2016.

Office Action from Chinese Patent Application No. 2017800570280, with English translation, dated Nov. 27, 2019; 22 pages.

Extended European Search Report for European Patent Application No. 17831608.9 dated Feb. 25, 2020.

Extended Euorpean Search Report for European Application No. 17831614 dated Mar. 18, 2020.

* cited by examiner

MEDICINE DELIVERY, WASH, CLEAN AND AIR DRY SYSTEM

CROSS-REFERENCE TO RELATED APPLICATIONS

This application claims benefit of U.S. provisional patent application Ser. No. 62/333,152, filed May 6, 2016, which is herein incorporated by reference.

BACKGROUND OF THE INVENTION

Embodiments of the present invention generally relate to apparatus and system for washing, cleaning, drying, and/or delivering medicine to a region of a human body. More specifically, aspects of the present invention provide a method and apparatus for delivering and applying water, medication, and/or a cleaning solution to a region of the body (e.g., genital or anal area, intimate parts, perineal region) which may be difficult for the user to access and dry the region.

DESCRIPTION OF THE RELATED ART

Bidets and other modern toilet seat systems have been used to spray water and clean private parts of a user using a toilet. The bidet systems are used for washing the genital and anal areas using cleaning water of appropriate temperature sprayed from the center of the bidet system, instead of a toilet paper after relief stool or urination. Originally being developed for washing the pubic area for females, bidet systems have now been popular among people of all ages and both sexes because it is known to be more hygienic to wash the intimate parts and anus with water instead of paper after relief. In addition, cleansing the pubic/anal regions with water may help to avoid infection and prevent hemorrhoids and other anal disease. Furthermore, it is very effective for women with gynecology diseases. It is also very useful for the elderly or obese people to relieve themselves with great convenience.

However, most bidets and bidet seat cleaning systems have water spray nozzle located to be positioned near posterior or anal area and thus not suitable for washing and cleaning female anterior private parts. In addition, bidet systems are expensive and need to be pre-installed. Further, the drying mechanisms of most bidets and bidet seat systems are not movable freely or localized to the area that need to be dried. Also, most bidets and bidet seat systems are not equipped with appropriate cleaning solutions or medications that are stored and delivered in mechanisms that can be freely movable or being localized to the area that need to be cleaned. Therefore, there is a need for a convenient, easy to carry wash and clean apparatus for cleaning genital or anal area of a human body.

SUMMARY OF THE INVENTION

The present invention generally includes a method and an apparatus for delivering medicine, washing, cleaning, and drying a region of a human body. In one embodiment, the apparatus includes a toilet seat assembly, a spraying nozzle assembly, a drying nozzle assembly, and a medicine delivery assembly. In another embodiment, a method of using a seat and cover system to deliver a solution to a region of a human body is provided and includes, washing an area of the region with a spraying nozzle assembly of the seat and cover system, cleaning the area of the region with the spraying nozzle assembly of the seat and cover system, drying the area of an drying nozzle assembly of the seat and cover system, and applying the solution onto the area using a medicine delivery assembly of the seat and cover system.

In still another embodiment, the toilet seat assembly of the invention includes a seat body, a seat housing, a base, and a seat cover. In addition, the spraying nozzle assembly includes one or more spray nozzle units comprising one or more spray nozzle bodies that are retractable and adapted to deliver a solution to the region of the human body, and a first driving motor being connected to the one or more spray nozzle units and adapted for moving the one or more spray nozzle bodies in retracting-and-extending motion, wherein the solution is selected form the group consisting of water, a cleaning solution, a barrier spray solution, a medicine-containing solution, and combinations thereof.

In one aspect, the spraying nozzle assembly further includes one or more steering gears, and a second driving motor being connected to the one or more spray nozzle unit and adapted for moving the one or more spray nozzle units in three-dimensional circular rotational motion. In another aspect, the one or more spray nozzle units of the spraying nozzle assembly includes a first spray nozzle channel adapted to deliver a first solution, and a second spray nozzle channel adapted to deliver a second solution, wherein the first solution is selected form the group consisting of water, a cleaning solution, a barrier spray solution, a medicine-containing solution, and combinations thereof, and wherein the second solution is selected form the group consisting of water, a cleaning solution, a barrier spray solution, a medicine-containing solution, and combinations thereof.

Further, in one aspect, the first spray nozzle channel is adapted to deliver water to the region of the human body for washing the region, and the second spray nozzle channel is adapted to deliver a cleaning solution to the region of the human body for cleaning the region. In another aspect, the second spray nozzle channel is adapted to deliver a medicine-containing solution to the region of the human body for treating the region.

In still another aspect, the first spray nozzle channel is connected to a first liquid line to deliver a washing solution to the region of the human body for washing the region, and the second spray nozzle channel is connected to a second liquid line to deliver a cleaning solution to the region of the human body for cleaning the region. In yet another aspect, the first spray nozzle channel is connected to a first liquid line to deliver a washing solution to the region of the human body for washing the region, and the second spray nozzle channel is connected to a second liquid line to deliver a medicine-containing solution to the region of the human body for treating the region.

In another embodiment, the medicine delivery assembly of the invention includes one or more medicine storage cartridges and the medicine delivery assembly is adapted to deliver one or more medicine-containing solutions that are stored at the one or more medicine storage cartridges. In yet another embodiment, the medicine delivery assembly is coupled to a spray nozzle channel of the spraying nozzle assembly.

Further, the medicine delivery assembly of the invention may include one or more driving motors, and a medicine delivery nozzle having a nozzle body that is retractable and is adapted to deliver the one or more medicine-containing solutions to the region of the human body, wherein the medicine delivery nozzle is separated from the spraying nozzle assembly.

In still another embodiment, the medicine delivery assembly may include one or more medicine base units, each medicine base unit having at least a cartridge unit and at least a cartridges slot, wherein the cartridge slot is adapted to match with a medicine storage cartridge, and wherein the medicine storage cartridge comprises a cartridge cover, a medicine inlet being connected to a medicine storage assembly, and a sensor. In one aspect, the medicine storage assembly includes a medicine storage tank adapted for storing a medicine-containing solution, a tank cover, and a tubing being connected to the medicine inlet of the medicine storage cartridge. In another aspect, the medicine storage assembly may further include a medicine storage element adapted to store one or more medicines to be mixed with water to form into the medicine-containing solution, and a liquid solution indicator adapted to indicate the content level of the medicine-containing solution within the medicine storage tank.

In yet another embodiment, the apparatus of the invention provides a drying nozzle assembly having one or more drying nozzle units comprising one or more retractable elements adapted to deliver air at a predetermined temperature to the region of the human body, and a fan connected to the one or more drying units. In one aspect, the drying nozzle assembly further includes a first driving motor being connected to the one or more drying nozzle units and adapted for moving the one or more retractable elements in retracting-and-extending motion, and a second driving motor being connected to the one or more drying nozzle unit and adapted for moving the one or more drying nozzle units in three-dimensional circular rotational motion.

In a further embodiment, the apparatus of the invention provides one or more control units adapted to receive a user input and, based on the user input, to direct movements of the first driving motor and the second driving motor and adjust the positions of one or more drying nozzle units within the drying nozzle assembly, wherein the one or more control units is selected from the group consisting of a remote control unit, a touch screen control unit, a joystick type control unit, a hand-held control unit, a steering-wheel type control unit, a built-in control unit adjacent the toilet seat assembly, and combinations thereof.

Accordingly, a method and apparatus that is easy to carry, easy to be connected to auxiliary parts, and easy to install and use is provided for washing, cleaning, drying, and delivering a medicine to a region of a human body. While the foregoing is directed to embodiments of the present invention, other and further embodiments of the invention may be devised without departing from the basic scope thereof, and the scope thereof is determined by the claims that follow.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. The drawings are not necessarily to scale. The drawings are merely schematic representations, not intended to portray specific parameters of the invention.

DETAILED DESCRIPTION

The present invention generally includes a method and a seat and cover system having a toilet seat assembly, a drying nozzle assembly, a spraying nozzle assembly, and a medicine delivery assembly for delivering and applying water, cleaning solutions, and/or medicines to a region of a human body that may not otherwise be easily accessible (e.g., to the perineal region), as well as washing and drying the region of the human body. In addition, a method of operating the seat and cover system is also provided.

Figure 1:
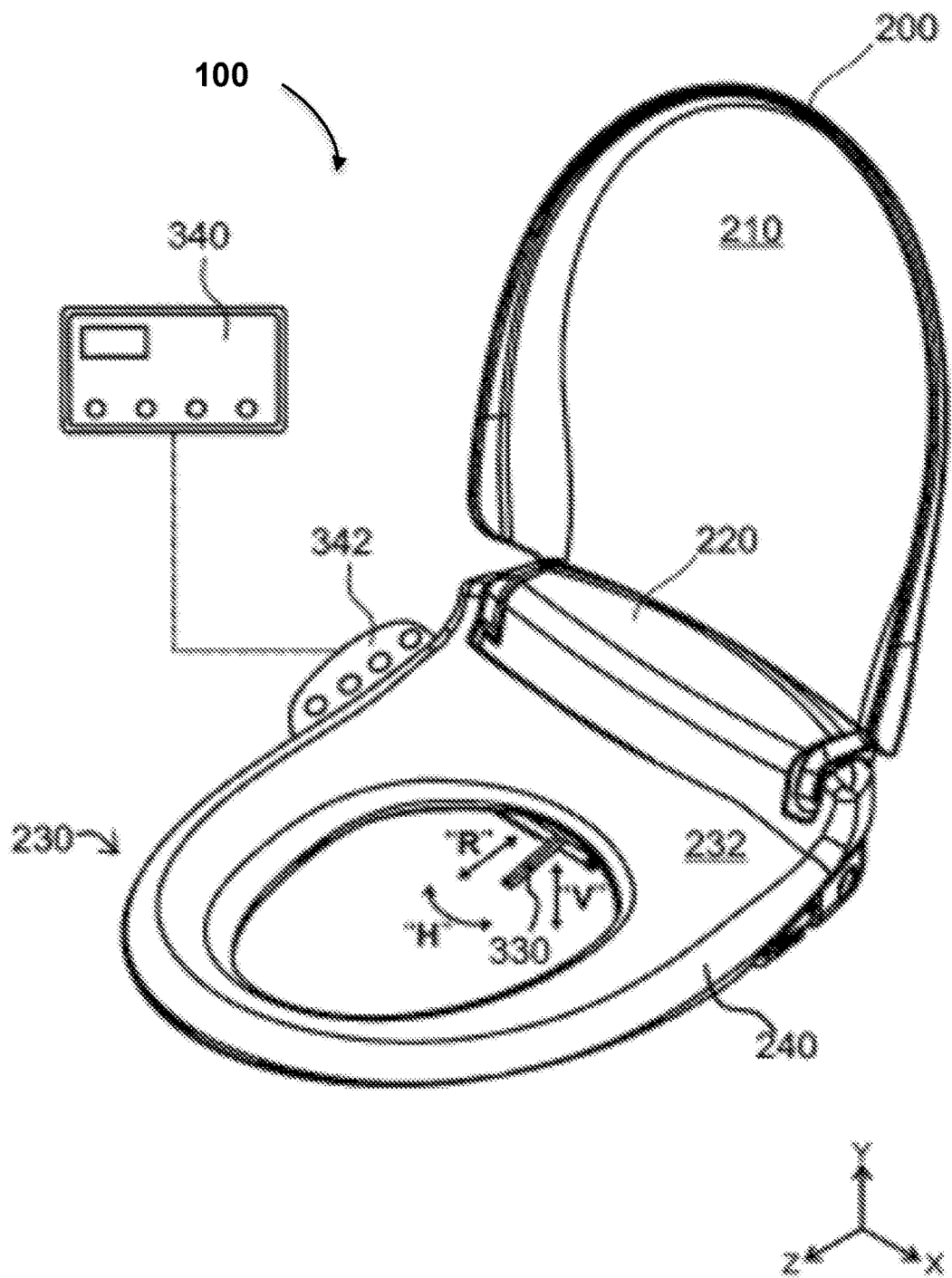
FIG. 1 is a perspective view of an example of a bidet seat system having a toilet seat assembly, a drying nozzle assembly, a spraying nozzle assembly, and a medicine delivery assembly according to embodiments of the invention.

FIG. 1 shows one example of a bidet seat and cover system, such as a bidet seat system 100. As shown in FIG. 1, the bidet seat system 100 may generally include a toilet seat assembly 200, a spraying nozzle assembly 300 having a spray nozzle unit 330, and one or more control units 340, 342. The bidet seat system 100 can be placed on top of a traditional toilet bowel with fitted sizes and shapes (oval or round). In one example, the toilet seat assembly 200 can be installed to a toilet system by removing any existing seat from a traditional toilet system and replacing a traditional seat with the bidet seat system 100. In another example, the bidet system 200 may have fastening elements (e.g., screws bolts, velcros, etc.) in its base to be connected to a traditional toilet bowel.

As shown in FIG. 1, the toilet seat assembly 200 includes a seat cover 210, a base housing 220, a seat 230 and a base 240. The seat cover 210 is generally closed to cover the base 240. During operation or in idle position, the seat cover can be opened and positioned upward, such as being positioned against a water tank. The seat 230 includes a seat body 232 facing upward so that a human subject can sit thereon.

The base housing 220 and the base 240 are formed to connect the seat cover 210 and the seat 230 together, for example, using one or more hinges such that the seat cover 210 can be opened or closed against the seat 230. The housing 220 and the base 240 are used generally to house one or more assemblies (e.g., the spraying nozzle assembly 300, a drying nozzle assembly 600, and a medicine delivery assembly 400, etc.) therein. As shown in FIG. 1, the spray nozzle unit 330 is adapted to be retractable and can be positioned inside the base housing 220 and extended out in a direction "R" to move in three dimensional rotational direction and in a horizontal plane "H". The spray nozzle unit 330 positioned near the bottom of the seat body 232 can be adjusted to be retracted back into the base housing 220.

In one embodiment, the function and operation of the bidet system 100 is controlled by one or more control units, such as a control unit 342 positioned adjacent to one side of the bidet system 100, and a controlled unit 340, which can be positioned at a distance away from the bidet system in a wired or wireless fashion. In FIG. 1, two control units 340, 342 are configured, where the control unit 342 is positioned to be adjacent the seat body 232 to be closer for a user to control the movements of the spray nozzle unit 330 of the spraying nozzle assembly 300 as well as the temperature and pressure of the spraying liquid spraying from the spray nozzle unit 330. Alternatively, the control unit 340 may be a remote controlled unit being capable of communicating with the bidet seat system 100.

The remote control units 340, 342 are adapted to be communicating and directing one or more movements of the spraying nozzle unit 330. The spray nozzle unit 330 is adapted to jet a solution, such as water or any liquid, a cleaning solution, a barrier spray solution, a medicine-containing solution, and combinations thereof to a localized region (e.g., perineal region) of a human body private part. In one example, the spray nozzle unit 330 is adapted to move in a direction marked as "R" to be extended and retracted in and out. In another example, the spray nozzle unit 330 is adapted to move in a vertical direction marked as "V" to move up and down (e.g., in a Z-direction or a gravitational direction), particularly after the spray nozzle unit 330 has been extended and retracted out. In another example, the spray nozzle unit 330 is adapted to move in a horizontal direction marked as "H" to move left-right, particularly after the spray nozzle unit 330 are extended and retracted out.

The remote control units 340, 342 can cause the user to operate the operation button reliably. The remote control units can provide "hands-free" options, therefore avoiding some discomfort or embarrassment from the user. For example, control units 340 can be mounted on the wall adjacent to or far away from the toilet. The control unit 340 has a screen and a keyboard with pushbuttons for turning the water or air on and off, for controlling the air temperature, etc. The water flow level may be selected by appropriate command through the remote control unit. The remote control unit is used to transit appliance control data to the bidet seat system 100. Inside the bidet seat system 100, a decoder decodes the transmitted data. When the data is decoded, the bidet seat system 100 responds to from an appliance control signal suitable for controlling the spraying nozzle assembly 300 and other parts within the bidet seat system 100. As another example, control units 342 can be mounted on the base 240. It enables a user to directly control the bidet seat system 100.

Figure 2:
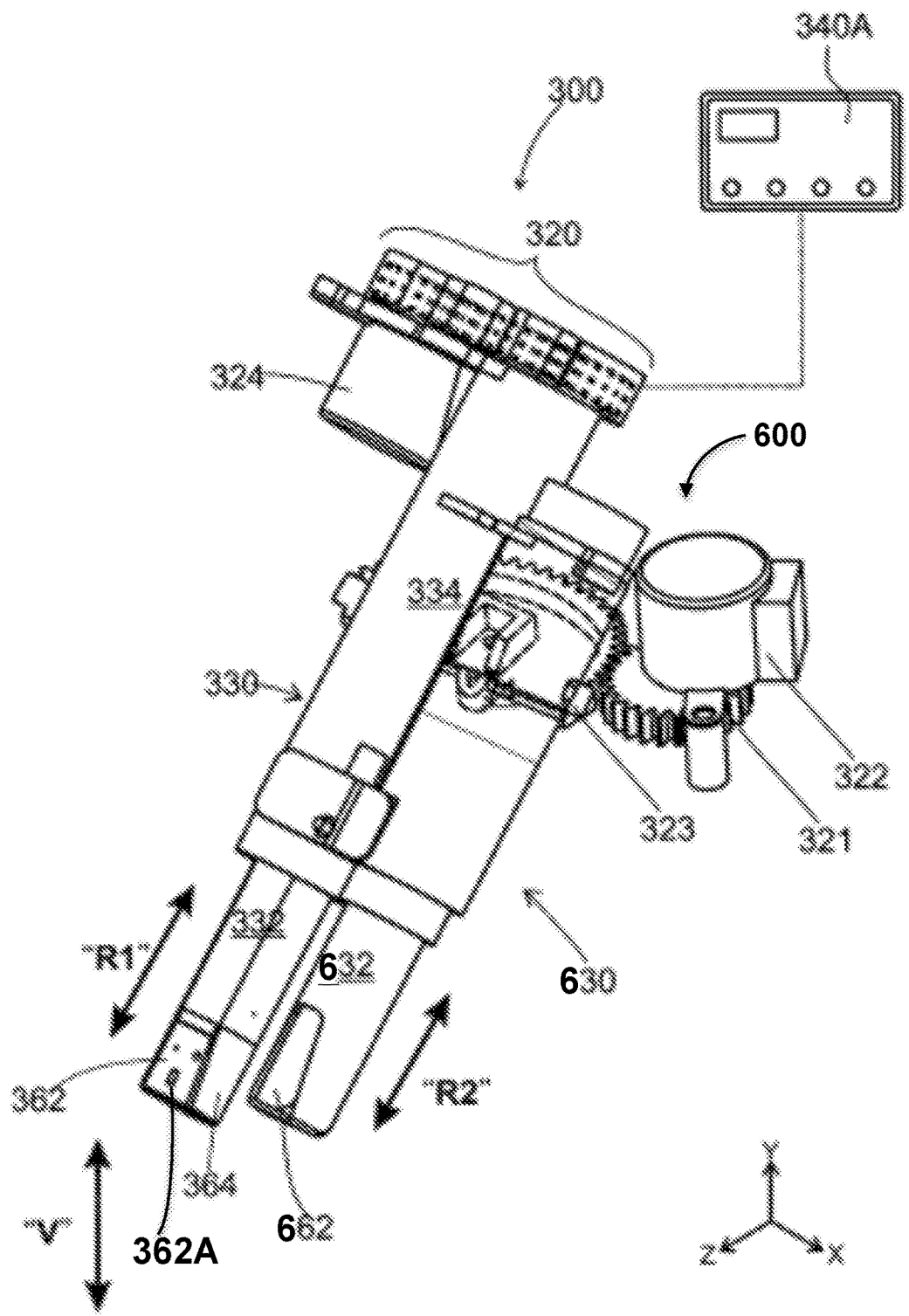
FIG. 2 illustrates one example of a bidet seat system having a drying nozzle assembly and a spraying nozzle assembly where their movements are controlled by a control unit connected thereto according to embodiments of the invention.

FIG. 2 shows one example of the spraying nozzle assembly 300 and the drying nozzle assembly 600, where their movements are controlled by a control unit 340A connected thereto. In one embodiment, the spraying nozzle assembly 300 includes a driving motor unit 320 to direct and drive the movements of the spray nozzle unit 330. The driving motor unit 320 is connected to a motor 324.

In another embodiment, the spray nozzle unit 330 includes one or more first spray nozzle bodies 332 and one or more second spray nozzle bodies 334, which are configured to function together and adapted to be retractable (as shown in a "R1" direction for extending and retracting movements) and movable in three-dimensional rotational motion, as driven by one or more driving motors (such as a driving motor 324, etc.) and steering gears (such as steering gears 321, 323, etc.) for delivering a solution therein.

Figure 4:
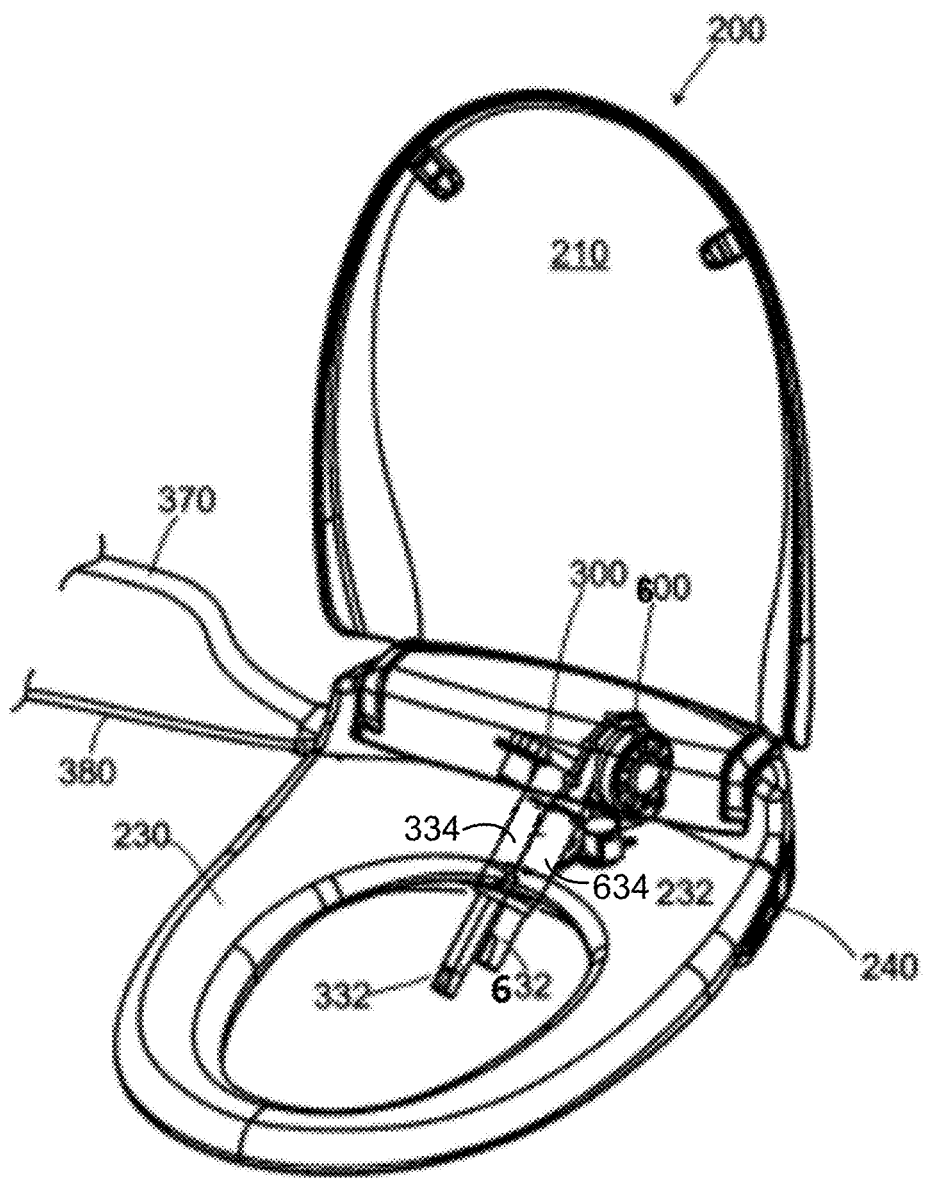
FIG. 4 shows another example of a bidet seat and cover system having two liquid lines connected to the spraying nozzle assembly according to embodiments of the invention.

Inside the first spray nozzle body 332 and the second spray nozzle body 334, there may be one, two or more spray nozzle channels, such as a first spray nozzle channel 362 and a second spray nozzle channel 364. Both of the first spray nozzle channel 362 and the second spray nozzle channel 364 are connected to the same or different liquid lines (such as liquid lines 370, 380 as shown in FIG. 4) for delivering one or more liquid solutions therein. Suitable solutions include water, a cleaning solution, a barrier spray solution, a medicine-containing solution, and combinations thereof. For example, medications, cleaning solutions, moisturizing creams, lotions, skin sealants, moisture barriers, skin protection paste, ointments, paste or solutions of mineral oil, silicone fluids (e.g. dimethicone and cyclomethicone), petrolatum, cod liver oil, lanolin, zinc oxide, talc, calamine, kaolin, topical starch and allantoin, lotions, fluids medicaments, skin protection fluid, chemical suspensions, and/or a pharmaceutical formulation to a surface area of a human subject. For example, Desitin® ointment (Pfizer, Inc.) is probably the most common topical used in treating diaper rash and other rashes. It contains common barrier materials (zinc oxide and petrolatum) and additionally contains two common skin conditioning agents (cod liver oil and lanolin).

Also shown in FIG. 2 is the drying nozzle assembly 600, which includes a drying nozzle unit 630 having a retractable element 634 and a nozzle tip portion 632. A drying nozzle opening is positioned at the tip of the nozzle tip portion 632. The retractable element 634 and the nozzle tip portion 632 of the drying nozzle unit 630 are configured to be retractable (as shown in a "R2" direction) and movable in three-dimensional rotational motion, as driven by one or more driving motors (such as a driving motor 638, etc.) and steering gears (such as a steering gears 321, 323, etc.).

In one embodiment, the movements of the spraying nozzle unit 330 and the drying nozzle unit 630 may be driven by separate set of motors and steering gears. In another embodiment, the movements of the spraying nozzle unit 330 and the drying nozzle unit 630 may be driven by a shared set or partially shared set of motors and steering gears. For example, as shown in FIG. 2, the driving motors 322, 324, may be coupled together by steering gears 321, 323 to function and drive coherently in order to coordinate and direct the movements of the spraying nozzle unit 330 and the drying nozzle unit 630.

The steering gears 321, 323 can rotate clockwise or counterclockwise. In one example, the driving motor unit 324 can be adapted to control the movements of the first spray nozzle body 332 and the second spray nozzle body 334 so that they are retractable, moving in a retractable direction, marked as "R1", to be extended and retracted in and out of the front end of the spray nozzle unit 330. In another example, the first spray nozzle body 332 and the second spray nozzle body 334 of the spraying nozzle unit 330 are configured to move in a vertical direction, marked as "V", to move up and down, particularly after the spraying nozzle unit 330 are extended and retracted out. In another example, the motor 324 can be adapted to control the movement of the nozzle tip portion 632 to be able to move in a retractable direction, marked as "R2", to be extended and retracted in and out of the front end of the drying nozzle unit 630.

Figure 3A:
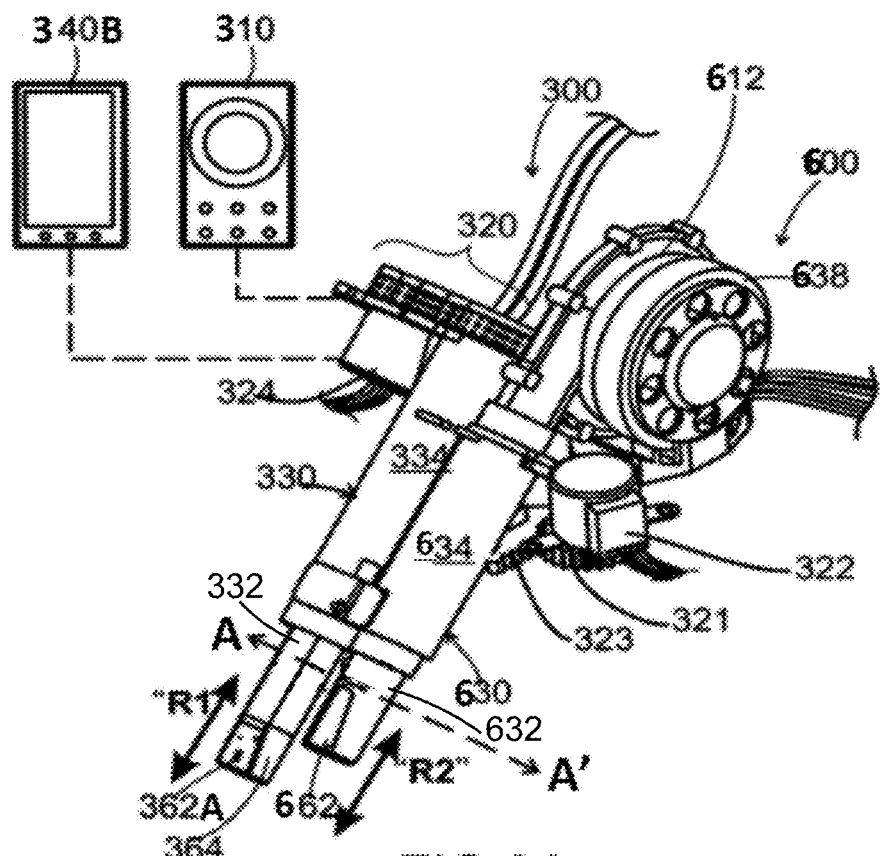
FIG. 3A illustrates another example of a bidet seat system having a drying nozzle assembly and a spraying nozzle assembly, and one or more remote control units according to embodiments of the invention.

FIG. 3A illustrates another example of the bidet seat system 100 having the spraying nozzle assembly 300, the drying nozzle assembly 600, and one or more control units 310, 340B. The bidet seat system include one or more motors 322, 324 that are coupled to function coherently by one or more gears 321, 323.

The control units 310, 340, 340A, 340B can be used for remotely controlling the spray nozzle assembly 300 and the drying nozzle assembly 600. In one embodiment, the control unit 340, 340A, 340B may include touch screen display that can detect one or more finger contacts. In other embodiments, the control units 310, 340, 340A, 340B may include control buttons, a joystick, a slider, a remote control unit, a hand-held control unit, a touch screen control unit, a joystick-type control unit, a steering-wheel type control unit, a built-in control unit being secured adjacent the toilet seat assembly, any other control device now known or later developed, and/or combinations. The remote control units 310, 340, 340A, 340B allows for the operation of devices that are out of convenient reach for direct operation of controls. The control units 310, 340, 340A, 340B can receive an input from a user of the bidet seat system 100 and transmits the user input to the responsible parts and components for the movements of the spray nozzle assembly 300 and the drying nozzle assembly 600.

Figure 3B:
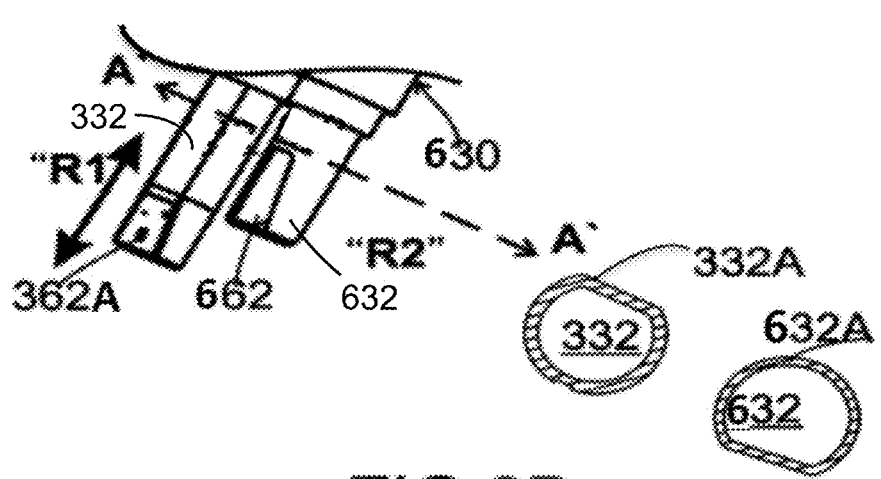
FIG. 3B is a partially enlarged view of a nozzle body and a nozzle jet head opening of the spraying nozzle assembly and a drying nozzle opening of the drying nozzle assembly of FIG. 3A and a cross-sectional view of the nozzle body of the spraying nozzle assembly and a nozzle tip portion of the drying nozzle assembly according to embodiments of the invention.

FIG. 3B is a partially enlarged view of the first spray nozzle body 332 and the nozzle jet head opening 362A of the spraying nozzle assembly 330 and the drying nozzle opening 662 of the drying nozzle assembly 630 of FIG. 3A and a cross-sectional view of the first spray nozzle body 332 of the spraying nozzle assembly 330 and the nozzle tip portion 632 of the drying nozzle assembly 630, cutting along the line A-A' according to embodiments of the invention, showing a wall 332A of the first spray nozzle body 332 and a wall 632A of the nozzle tip portion 632.

FIG. 4 shows another example of the toilet seat assembly 200. In one embodiment, the toilet seat assembly 200 is connected with the liquid lines 370, 380 for a source of hot water and a source of cold water, and for a cleaner solution or medicine-containing solution. In another embodiment, the toilet seat assembly 200 is connected with the liquid lines 370, 380 and capable of jetting water or delivering a medicine-containing solution.

Figure 5A:
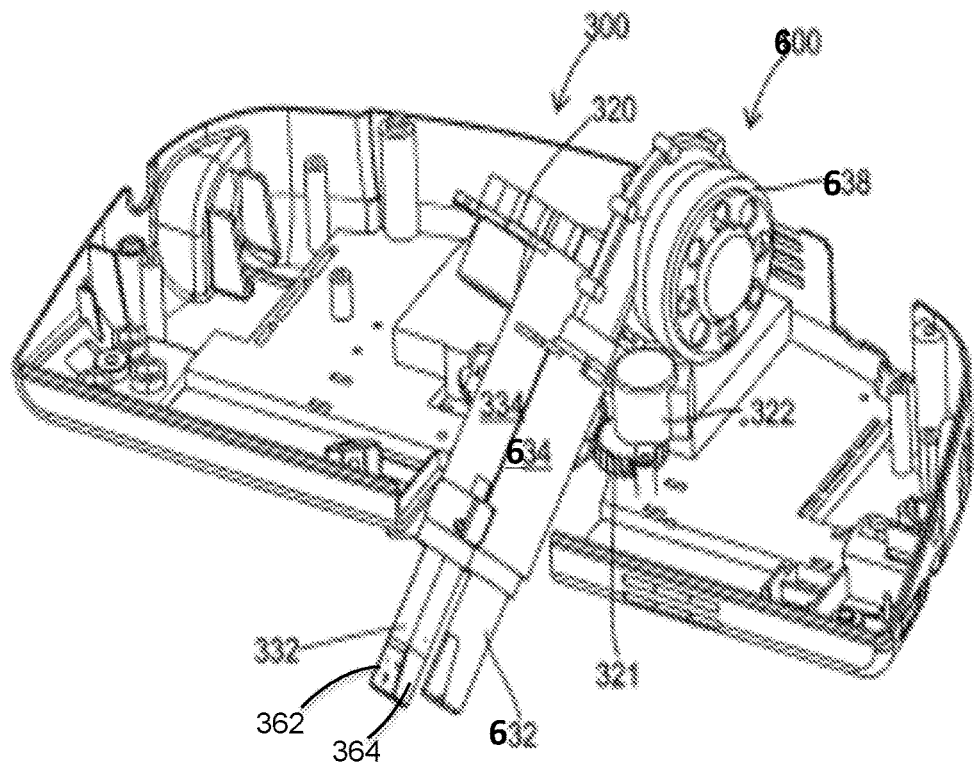
FIG. 5A is an internal perspective view of one example of a base housing of a toilet seat assembly to illustrate inside views of a spray nozzle assembly and a dry nozzle assembly according to embodiments of the invention.
Figure 5B:
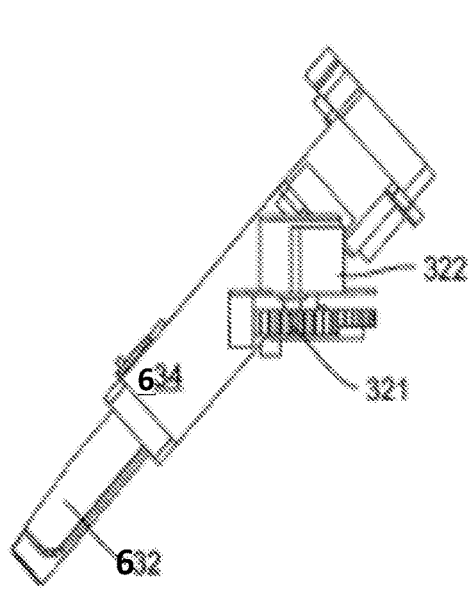
FIG. 5B is a partially enlarged side view of the drying nozzle assembly of FIG. 5A according to embodiments of the invention.
Figure 5C:
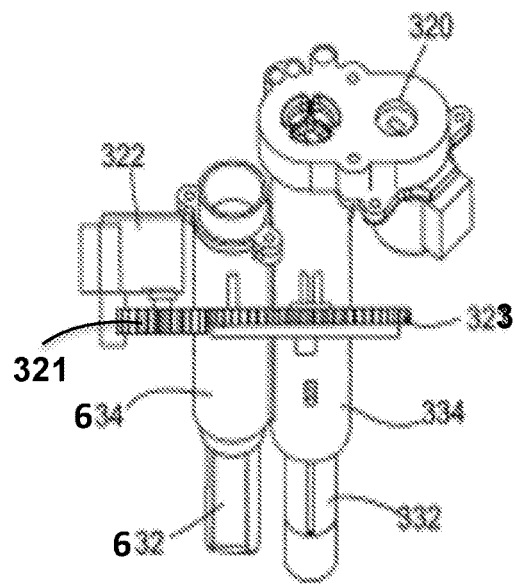
FIG. 5C is a partially enlarged bottom view of the spray nozzle assembly and the drying nozzle assembly of FIG. 5A according to embodiments of the invention.

FIG. 5A shows an internal perspective view of the base housing 210 of the toilet seat assembly 200 to illustrate inside views of the spray nozzle assembly 300 and the dry nozzle assembly 600. The spraying nozzle unit 330 may include the first spray nozzle body 332, the second spray nozzle body 334, whose movements are driven by the driving motor units 320, 322. FIG. 5B is a partially enlarged side view of the drying nozzle assembly 600 of FIG. 5A and FIG. 5C is a partially enlarged bottom view of the spray nozzle assembly 300 and the drying nozzle assembly 600 of FIG. 5A. As shown in FIGS. 5A-5C, the driving motor units 320, 322 may be coupled together by one or more steering gears 321, 323 in order to coordinate and direct the movements of the spray nozzle assembly 300 and the drying nozzle assembly 600.

Figure 6:
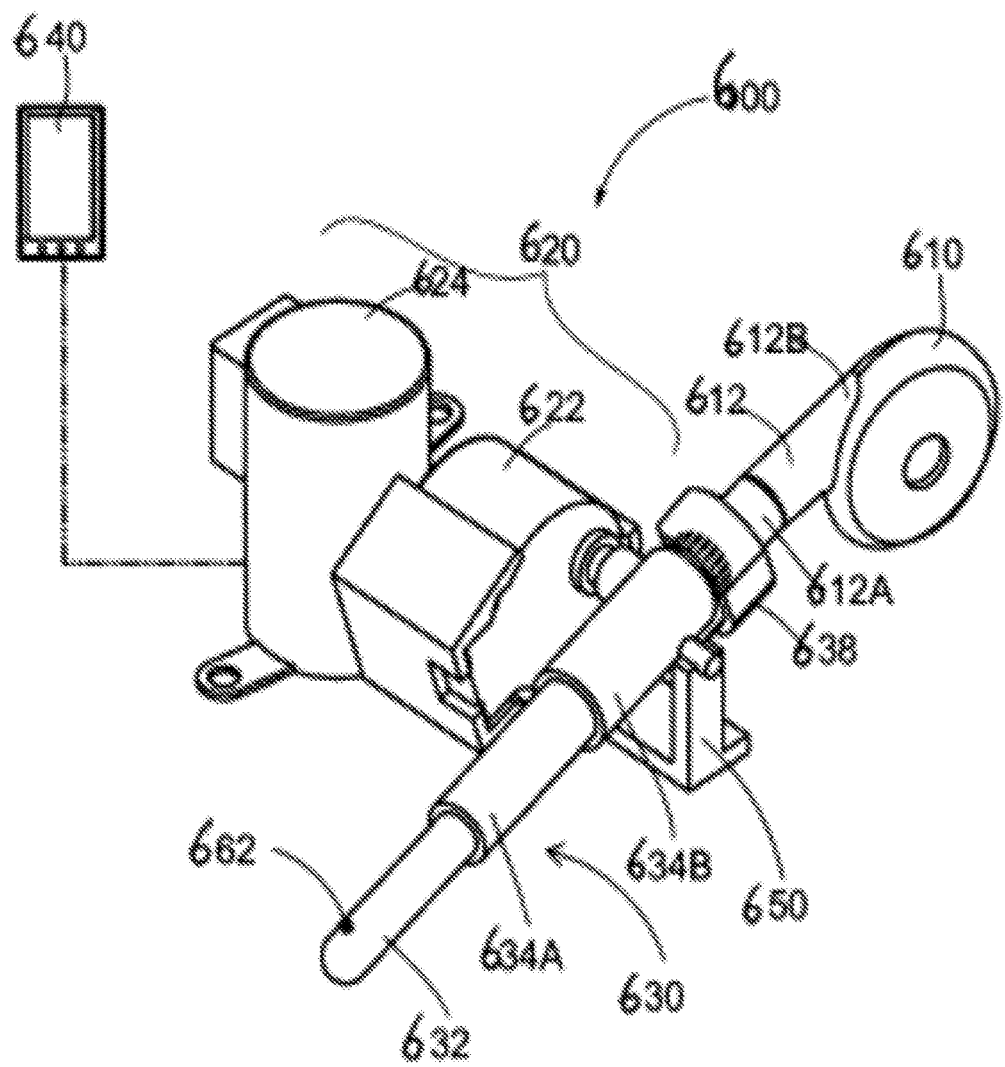
FIG. 6 illustrates one example of a dry nozzle assembly being adapted to communicate with a remote control unit according to embodiments of the invention.

FIG. 6 illustrates the movements of the drying nozzle assembly 600 as driven by one or more motors, such as a driving motor assembly 620 having driving motors 622, 624, as connected and coupled by a connector base 650. The driving motors 622, 624 can be controlled by a control unit 640 (via wired or wireless connection) in order to coordinate and direct the movements of the drying nozzle assembly 600.

In one embodiment, the drying nozzle unit 630 includes a fan 610, one or more air channels 612, 612A, 612B, retractable elements 634, 634A, 634B, 634C, and a nozzle tip portion 632, with the drying nozzle opening 662 located at the tip. The drying nozzle unit 630 may be able to deliver air with the use of a high output power fan, such as the fan 610. In one embodiment, the fan 610 of the drying nozzle assembly 600 is adapted to blow air at an adjustable speed. In another aspect, the fan 610 of the drying nozzle assembly 600 is adapted to blow air at an adjustable temperature.

Figure 7:
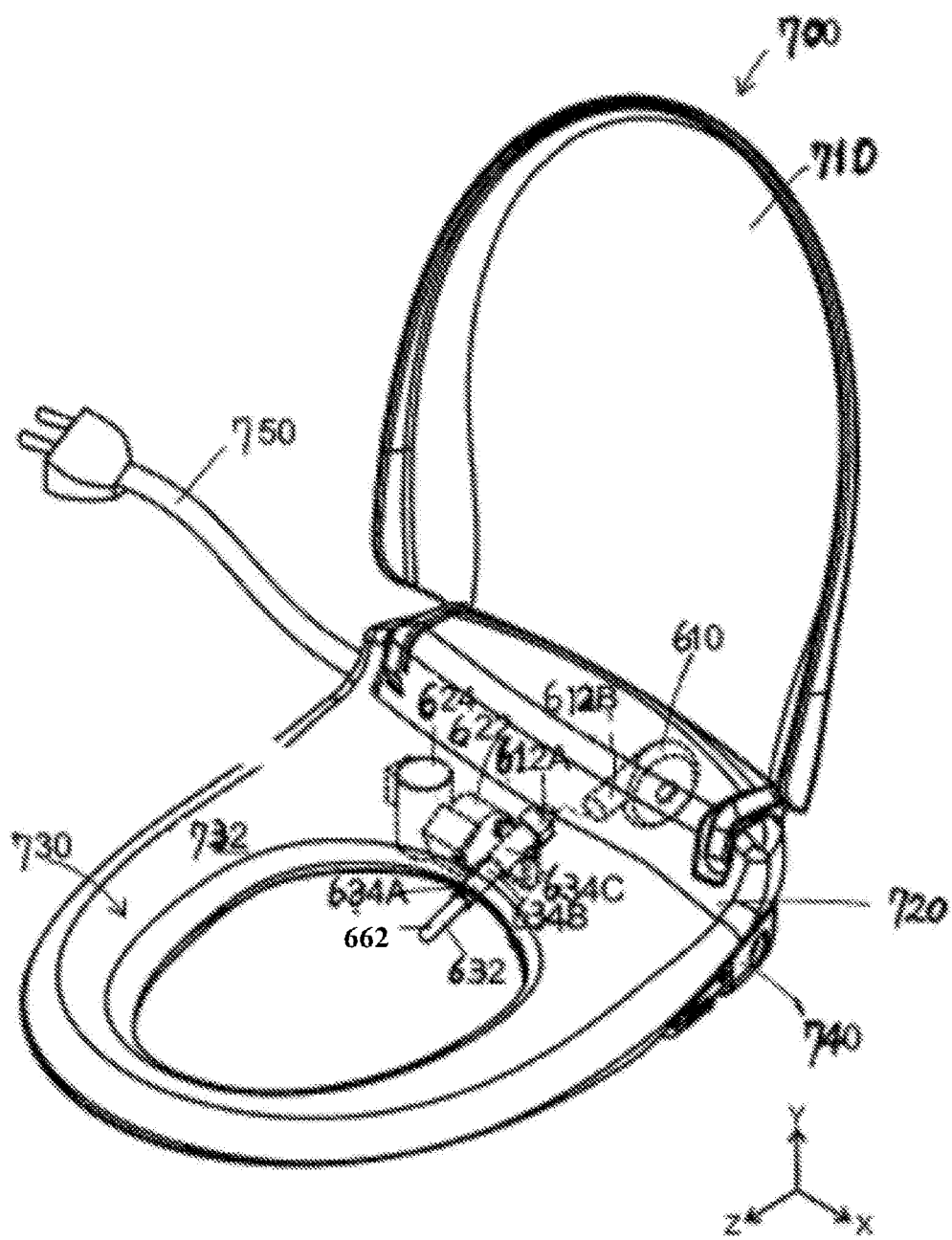
FIG. 7 is an internal perspective view of one example of a base housing of a bidet seat and cover system to illustrate the inside views of a dry nozzle assembly according to embodiments of the invention.

FIG. 7 is an internal perspective view of a base housing 720 of a toilet seat assembly 700 to show the inside views of the drying nozzle assembly 600. The toilet seat assembly 700 includes a seat cover 710, the base housing 720, a seat 730, a seat body 732, a base 740, and an electric wire 750. The toilet seat assembly 700 is connected, via the electric wire 750, to an electric outlet to provide electric driving power to various motors and fans within the toilet seat assembly 700.

Figure 8:
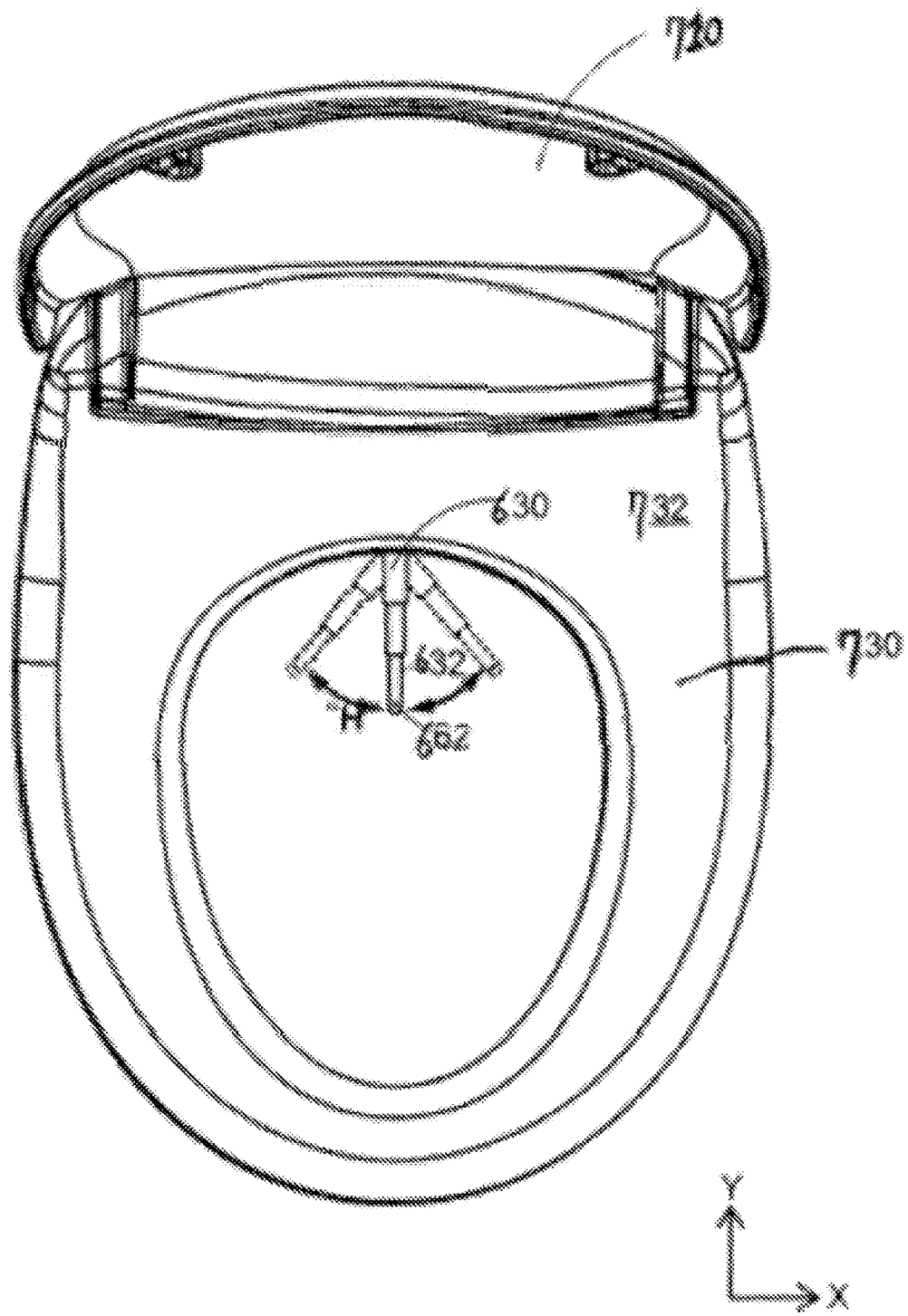
FIG. 8 is a top view of the bidet seat and cover of FIG. 7, showing the three-dimensional rotational movements of a drying nozzle assembly according to embodiments of the invention.

FIG. 8 shows a top view of the drying nozzle unit 630 stored inside the seat body 730 within the seat 730. Under the control of a user, the drying nozzle assembly 630 may extend the nozzle tip portion 632 out so as to blow air out of the drying nozzle opening 662 and dry an area or a region of a body part of a human subject. In addition to being retractable, the drying nozzle unit 630 is adapted to move in three-dimensional direction, both vertically, horizontally, and circularly (as marked in an arrowed direction "H" (e.g., circular, or rotational, in three-dimensional, etc.) so as to be able to reach to a localized area near a region of a human body that need to be dried.

Figure 9:
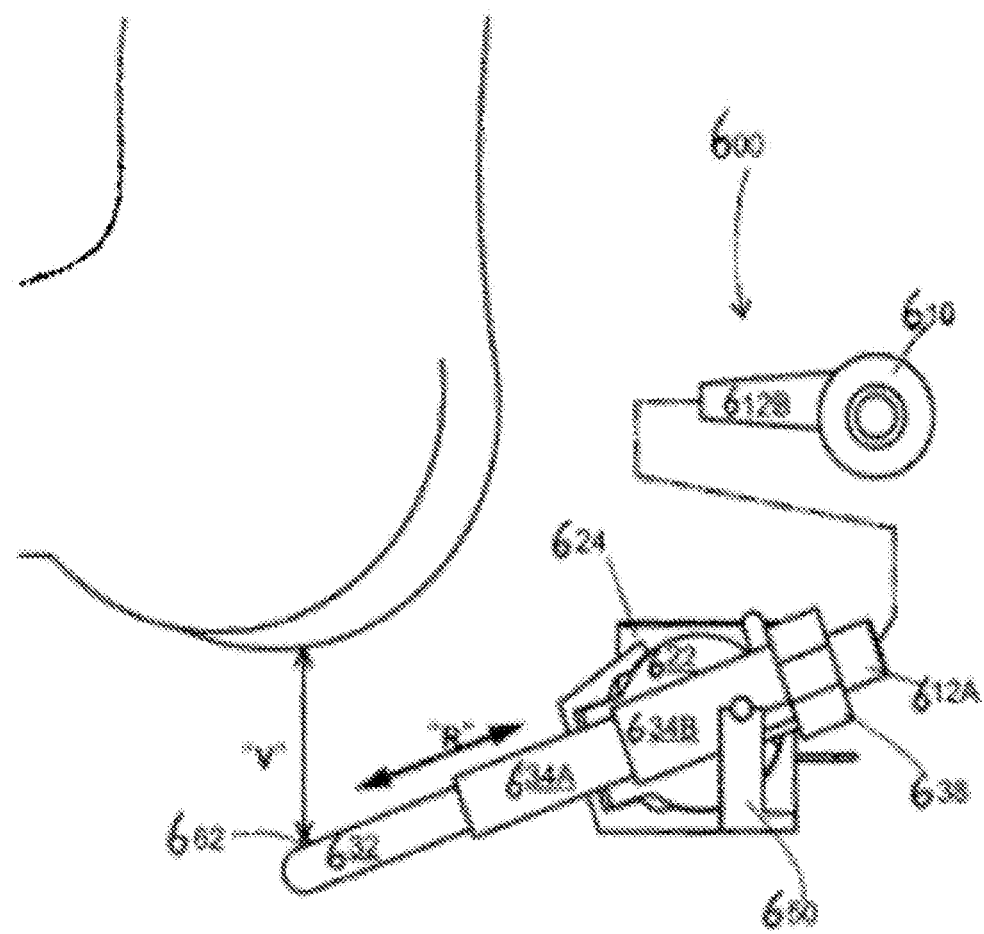
FIG. 9 is a side view showing one example of a drying nozzle assembly according to embodiments of the invention.

FIG. 9 is a side view showing a human subject using the drying nozzle assembly 600 according to embodiments of the invention. In one example, driving motors 622, 624 can be adapted to control the movements of the nozzle tip portion 632 to be able to move in a retractable direction, marked as "R", to be extended and retracted in and out of the front end of the drying nozzle assembly 600. In another example, the drying nozzle assembly 600 are able to move in a vertical direction, marked as "V", to move up and down, particularly after the drying nozzle assembly 600 are extended and retracted out.

Figure 10A:
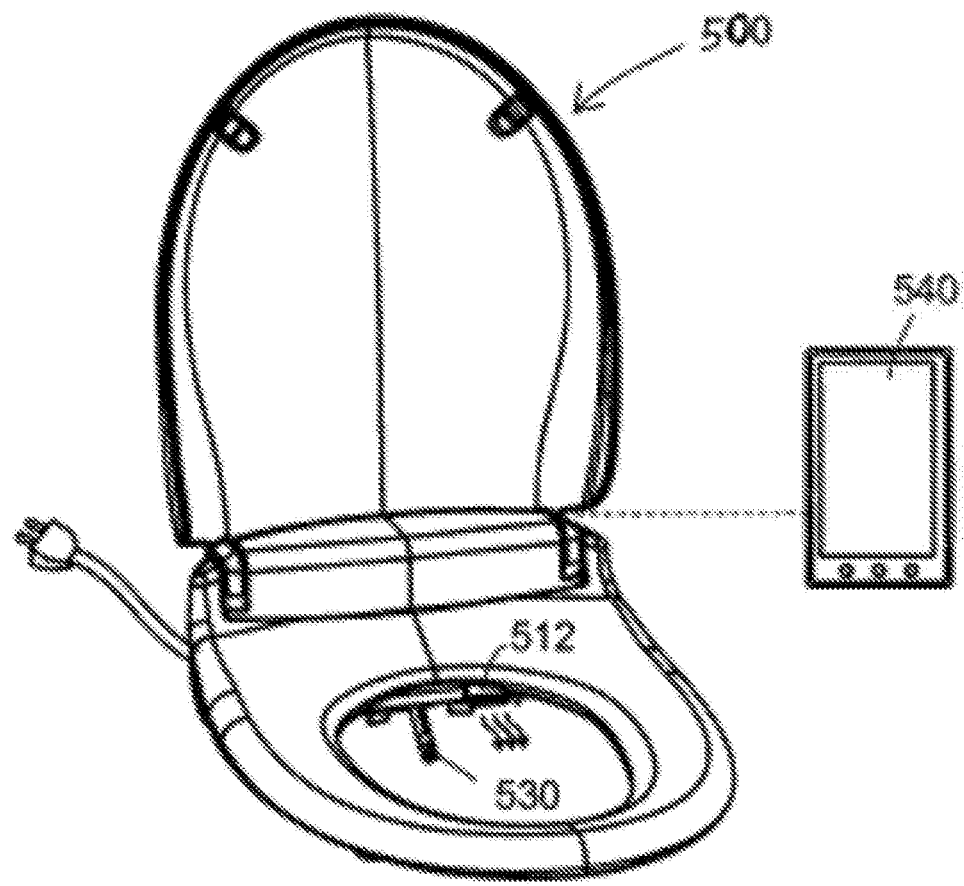
FIG. 10A is a perspective view of a prior-art conventional bidet seat system having a bidet toilet seat, a prior-art air vent, and a prior-art retractable-only spray nozzle mechanism.
Figure 10B:
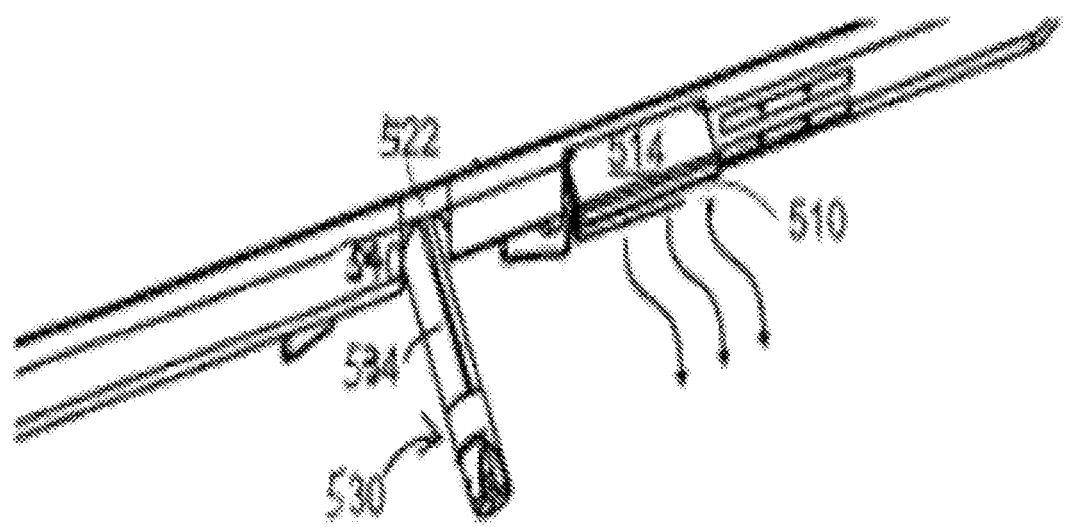
FIG. 10B is a partially enlarged view of a prior-art air vent and the prior-art retractable-only spray nozzle mechanism of FIG. 10A.

FIG. 10A is a perspective view of a prior-art conventional bidet seat system having a bidet toilet seat assembly 500, an air vent 512, and a spray nozzle mechanism 530. FIG. 10B is a partially enlarged view of the air vent 512 and the spray nozzle mechanism 530 of FIG. 10A. The air vent 512 generally includes a fan cover 514 and a plurality of leaves 510 to direct the direction of air flow (the leaves are used to direct air flow, similar to leaves on a small single-room air conditioner). The spraying nozzle mechanism 530 may include a cut-out 522 near a covering 540, where a spray nozzle 534 can extended out. The angles and movements of the spraying nozzle mechanism 530 and the air vent 512 are limited and usually are extended out downward and cannot be controlled to a desired area of a human body. They cannot be extending or retracting, in combination with raising up or lowering the angle to be near a region of the body of a user.

Figure 11:
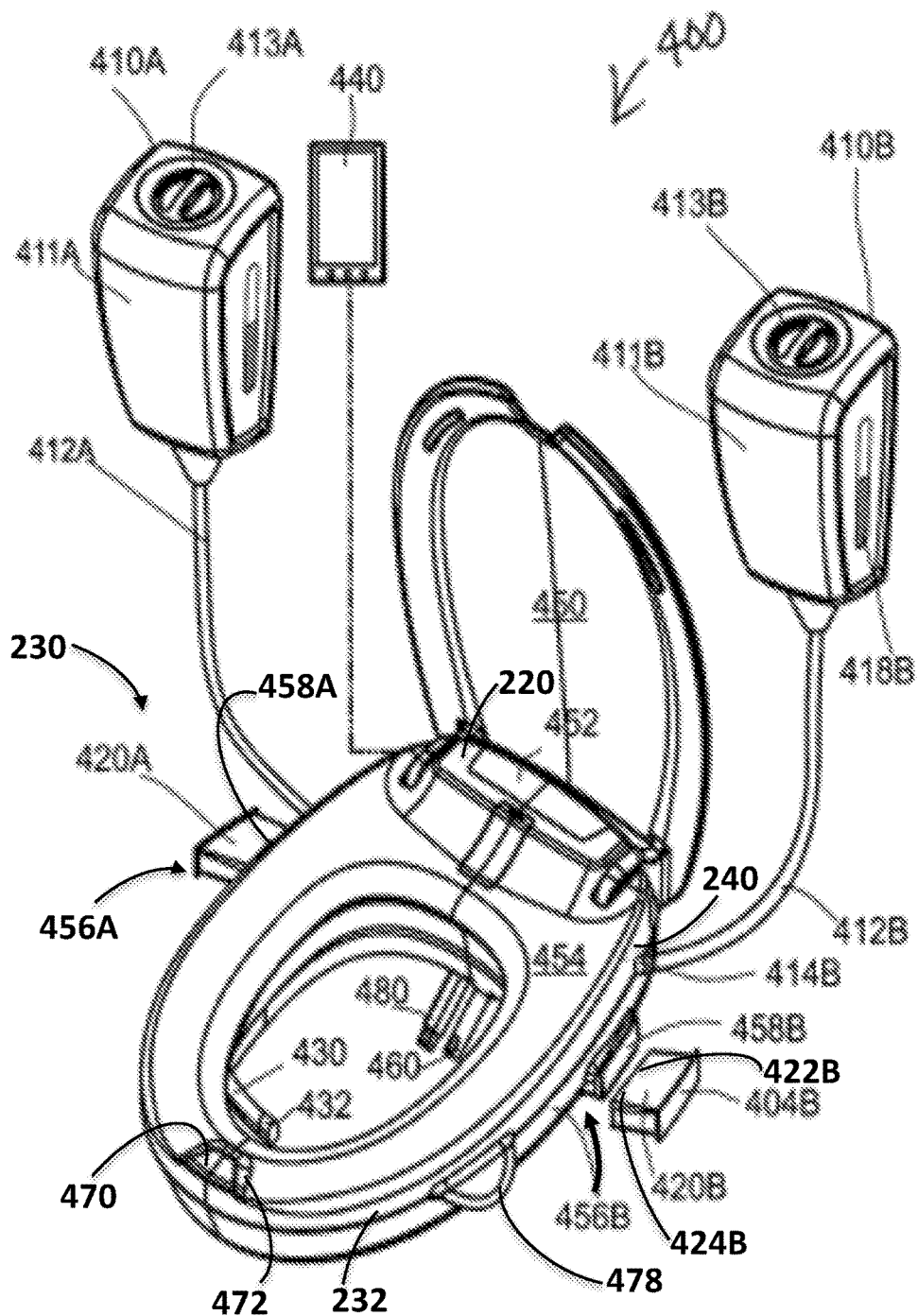
FIG. 11 shows one example of a medicine delivery assembly in conjunction with a spraying nozzle assembly and a drying nozzle assembly as controlled by a control unit remotely according to embodiments of the invention.

FIG. 11 shows one example of a medicine delivery assembly 400 in conjunction with a spraying nozzle assembly 480 and a drying nozzle unit 460 as controlled by a control unit 440 remotely according to embodiments of the invention. In one embodiment, the medicine delivery assembly 400 may include one or more medicine storage assembly 410A, 410B for delivering a solution, such as a medicine-containing solution (e.g., zinc oxide, menthol-containing solutions, silicone fluids (e.g. dimethicone and cyclomethicone), petrolatum, cod liver oil, lanolin, zinc oxide, talc, calamine, kaolin, topical starch and allantoin, lotions, fluids medicaments, skin protection fluid, etc.) The medicine storage assembly 410A, 410B may each include a medicine storage tank 411A, 411B, adapted for storing a medicine-containing solution, a tank cover 413A, 413B, a tubing 412A, 412B, and a pipe orifice 414A, 414B connected to the base 240 to go to the inside of the base housing 220.

In another embodiment, the medicine delivery assembly 140 can include one or more medicine storage cartridges, such as medicine storage cartridges 420A, 420B, and the medicine delivery assembly 140 is adapted to deliver e one or more medicine-containing solutions that are stored at the medicine storage cartridges 420A, 420B. Once medicine-containing solution within the medicine storage cartridges 420A, 420B are low or empty, they can be easily replaced with a new set of matching medicine storage cartridges 420A, 420B.

In still another embodiment, the medicine delivery assembly 140 includes one or more medicine base units, such as a right medicine base unit 456A and/or a left medicine base unit 456B, etc. Each medicine base unit 456A, 456B includes at least a cartridge unit 428A, 428B, and at least a cartridges slot 458A, 458B, where each of the cartridge slot 458A, 458B is adapted to match with a medicine storage cartridge, such as medicine storage cartridge 420A, 420B.

In one aspect, each of the medicine storage cartridge 420A, 420B includes a cartridge cover 404A, 404B, a medicine inlet 422A, 422B being connected to a medicine storage assembly (such as the medicine storage assembly 410A, 410B or any other suitable medicine storage assembly, positioned within the base housing 220), and a sensor 429A, 429B for matching and identifying a medicine solution stored within the medicine storage assembly.

Figure 13:
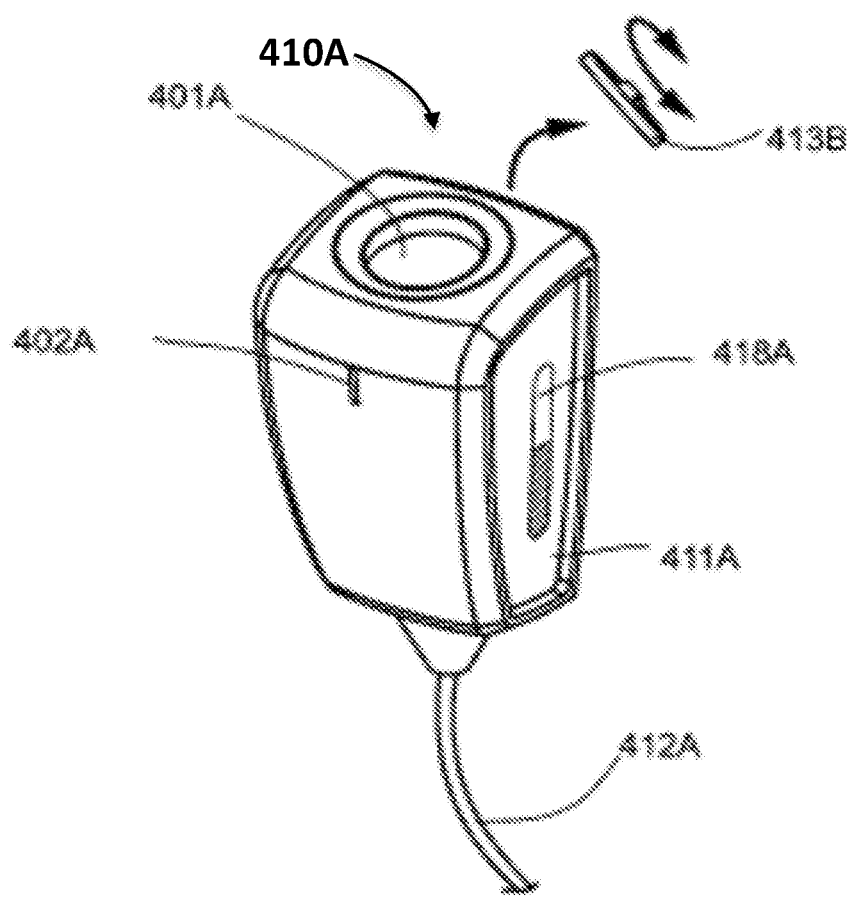
FIG. 13 illustrates one example of a medicine storage assembly according to embodiments of the invention.

FIG. 13 shows one example of the medicine storage assembly 410. The tank cover 413B of the medicine storage assembly 410A can be opened and closed by clockwise or counterclockwise movements. The medicine storage tank 411A is adapted for storing a medicine-containing solution. In one example, the tubing 412A is connected to the medicine inlet 422A of the medicine storage cartridge 420A. In another example, the medicine storage assembly 410A, 410B further includes a medicine storage element 402A, 402B, which is adapted to store one or more medicines to be mixed with water to form into the medicine-containing solution.

In another example, the medicine storage assembly 410A, 410B further includes a liquid solution indicator 418A, 418B adapted to indicate the content level of the medicine-containing solution within the medicine storage tank 411A, 411B. Further, the medicine storage assembly 410A, 410B may also include a pressurized pump 415A, 415B adapted to pump and deliver the medicine-containing solution from the medicine storage tank 411A, 411B into the toilet seat assembly 200.

Figure 14:
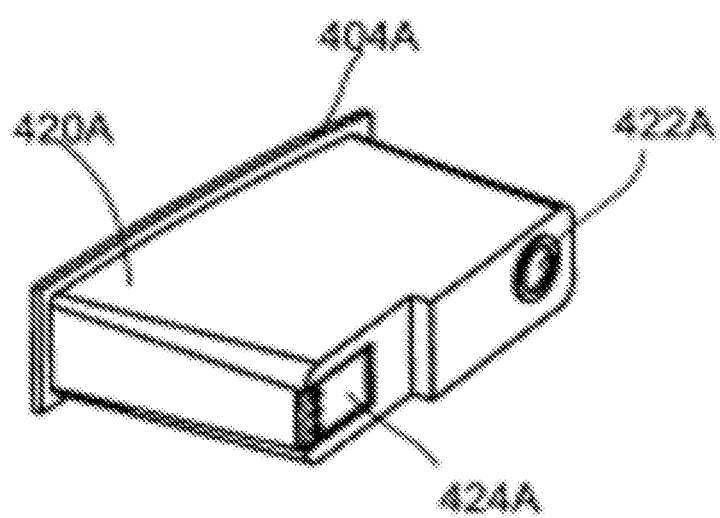
FIG. 14 illustrates one example of a medicine storage cartridge of a medicine base unit according to embodiments of the invention.

FIG. 14 illustrates detail of the medicine storage cartridge 420A, which is coupled to a sensor 424A to indicate the current status of a medicine-containing solution stored therein. The medicine storage cartridges 420A, 420B can be pulled out from the cartridge slot 458B for adding or changing medicines.

Referring back to FIG. 12, which shows an internal perspective view of another example of the base housing 220 of the bidet seat and cover system 100 to illustrate interior views of the spraying nozzle assembly, the drying nozzle assembly, and the medicine delivery assembly 400, showing more than one suitable medicine base units (such as the right medicine base unit 456A and the left medicine base unit 456B), more than one medicine storage cartridges 420A, 420B, and a medicine delivery nozzle 430 according to embodiments of the invention.

Figure 12:
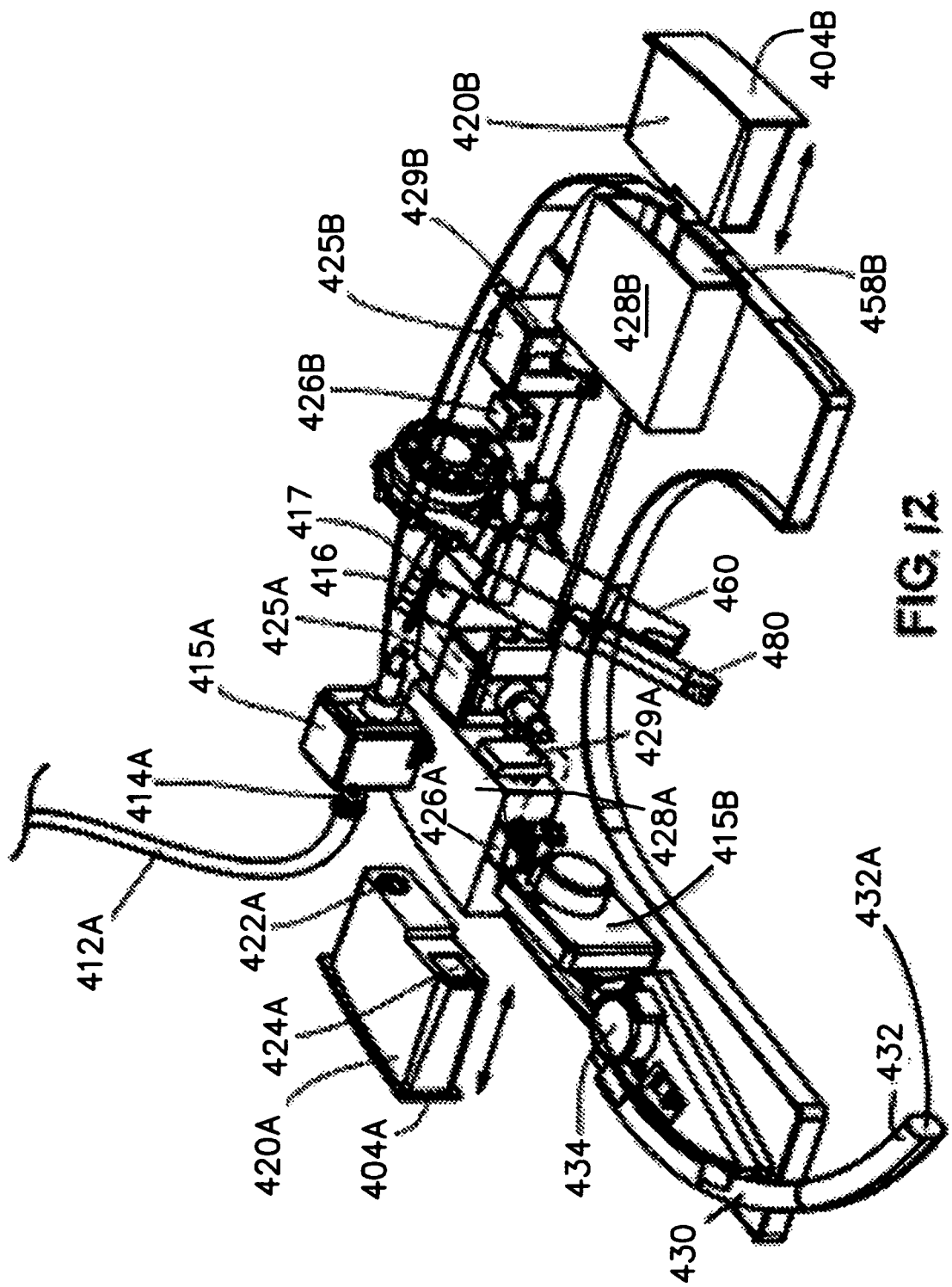
FIG. 12 is an internal perspective view of another example of a base housing of a bidet seat and cover system to illustrate interior views of a spraying nozzle assembly, a drying nozzle assembly, and a medicine delivery assembly, showing more than one suitable medicine base units, medicine storage cartridges, and a medicine delivery nozzle according to embodiments of the invention.

As shown in FIG. 12, the medicine delivery assembly 400 can include one or more driving motors 426A, 426B, one or more steering gears 416, and a medicine delivery nozzle 430 having a nozzle body 432 that is adapted to be retractable and movable rotationally and vertically in three-dimensional direction. In one embodiment, the medicine delivery nozzle 430 is adapted to deliver one or more medicine-containing solutions to the region of the human body.

In one aspect, the medicine delivery nozzle 430 includes an atomizer nozzle head 432A adapted to atomize a medicine-containing solution to achieve a consistency that can be applied over a distance and deliver a stream of the medicine-containing solution to a user. In another aspect, the medicine delivery nozzle 430 is adapted to deliver the medicine-containing solutions across a space to a perineal region of a user. In still another aspect, the medicine delivery assembly 400 further includes a pressurized pump 425A, 425B adapted to pump and deliver the medicine-containing solution from the medicine inlet 422A, 422B of the medicine storage cartridge 420A, 420B.

Figure 15A:
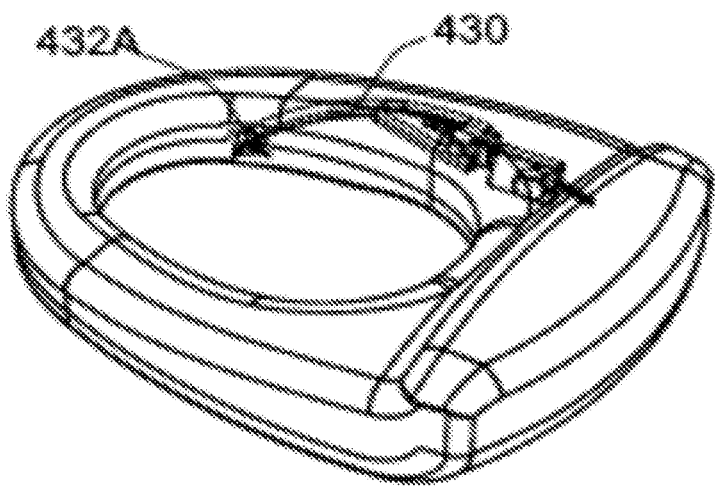
FIG. 15A is an internal perspective view of a medicine delivery assembly, showing one example of a medicine delivery nozzle the according to embodiments of the invention.

In still another embodiment, the spraying nozzle assembly 480 and the medicine delivery nozzle 430 of the medicine delivery assembly 400 may be adapted to be able to move similarly in three-dimensional dynamic movements, but be separated physically from each other to work together in spraying a solution and delivering a medicine-containing solution, respectively. FIG. 15A is an internal perspective view of the medicine delivery assembly 400, showing one example of the medicine delivery nozzle 430 that works independently in delivering a medicine-containing solution without going through the spraying nozzle assembly 400 positioned near base housing 220.

Figure 15B:
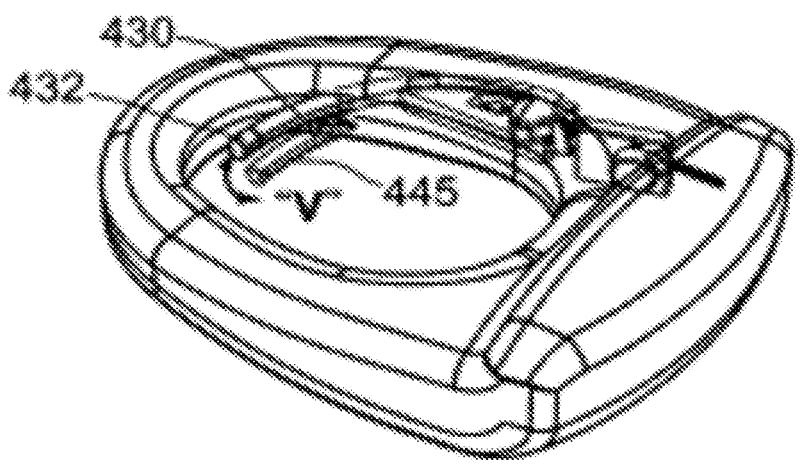
FIG. 15B illustrates vertical movements of the medicine delivery nozzle of the medicine delivery assembly of FIG. 15A.

FIG. 15B illustrates vertical movements of the medicine delivery nozzle 430 of the medicine delivery assembly 400 of FIG. 15A. The medicine delivery nozzle 430 is adapted to move in a vertical and/or rotational direction, marked as "V", to move up and down, particularly after the medicine delivery nozzle 430 are extended out, not retracted.

Figure 15C:
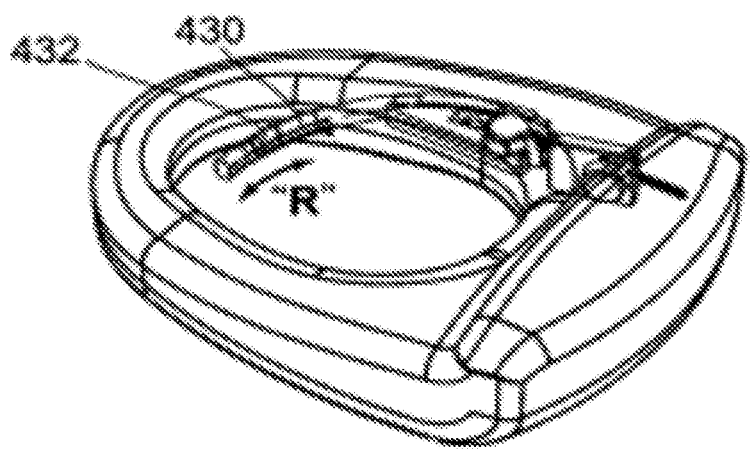
FIG. 15C illustrates retracting and extending movements of the medicine delivery nozzle of the medicine delivery assembly of FIG. 15A.

FIG. 15C illustrates the retracting and extending movements of the medicine delivery nozzle 430 of the medicine delivery assembly 400 of FIG. 15A. The medicine delivery nozzle 430 is adapted to move in a retractable direction, marked as "R", to be retracted in and extended out of the front end of the medicine delivery nozzle 430.

In one embodiment, the medicine delivery assembly 400 may be adapted to couple to and function together to deliver a medicine-containing solution to the one or more spray nozzle channels of the spraying nozzle assembly 300 and/or the spraying nozzle assembly 480. In one aspect, the spray nozzle channels of the spraying nozzle assembly 300, 480 includes the nozzle jet head opening 362A adapted to deliver any suitable solution at high speed. Suitable solution may be selected form the group consisting of water, a cleaning solution, a barrier spray solution, a medicine-containing solution, and combinations thereof.

Figure 16:
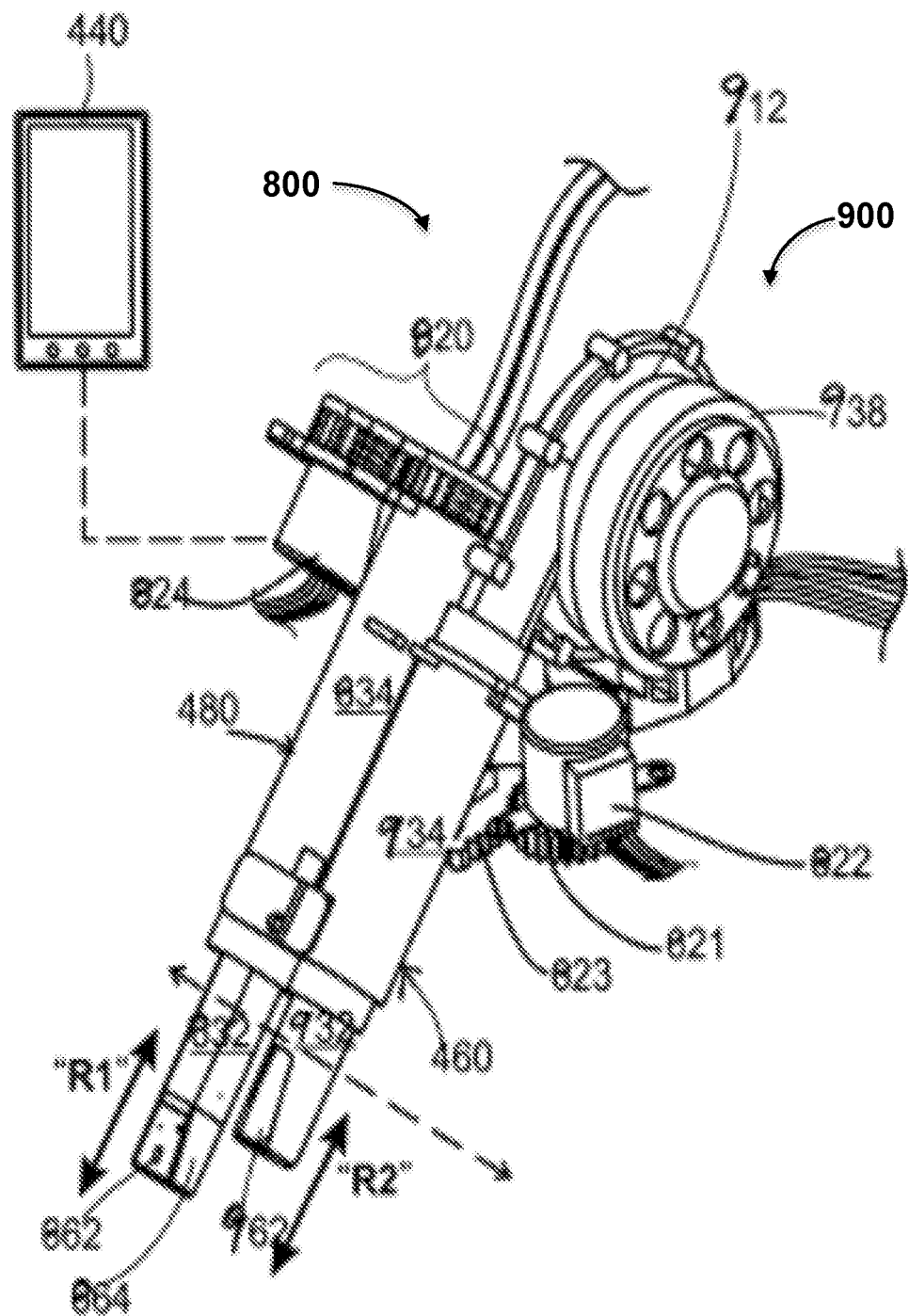
FIG. 16 illustrates another example of a spray nozzle assembly, a drying nozzle assembly as controlled according to embodiments of the invention.

FIG. 16 illustrates another example of a spraying nozzle assembly 800, a drying nozzle assembly 900 as controlled a control unit 440. The spraying nozzle assembly 800 includes a nozzle body 834 and a nozzle tip portion 832, and their movements are driven by one or more driving motor unit 820 with one or more driving motor 822, 824, which are coupled to steering gears 821, 823 to function together. Two nozzle channels with nozzle tip openings 862, 864 are configured inside the nozzle body 834 for separately delivering water and a cleaning solution in each nozzle channel. Alternatively, the two nozzle channels may be configured to deliver water and a medicine-containing solution each.

The drying nozzle assembly 900 includes a fan 938, one or air channels 912 connected to the fan 938, one or more drying nozzle units 460 connected to the one or more air channels 912, and one or more driving motor units 820 with driving motor 822, 824, which are shared with the spraying nozzle assembly 800 so that the spraying nozzle assembly 800 and the drying nozzle assembly 900 can be coupled to move together. In one aspect, the one or more driving motor units 820 of the drying nozzle assembly 900 includes one or more steering gears, a first driving motor being connected to the one or more drying nozzle units and the one or more steering gears, wherein the first driving motor is adapted to move the one or more drying nozzle units in retracting-and-extending motion. In another aspect, the one or more driving motor units of the medicine delivery assembly further includes a second driving motor being connected to the one or more drying nozzle units and the one or more steering gears, wherein the second driving motor is adapted to move the one or more drying nozzle units in three-dimensional circular rotational motion.

Another embodiment of the invention provides one or more control units connected to the toilet seat assembly and the medicine delivery assembly, where the control units are adapted to receive a user input and, based on the user input, to direct movements of one or more motors and adjust the positions of one or more nozzles within the toilet seat assembly and the medicine delivery assembly.

Figure 17:
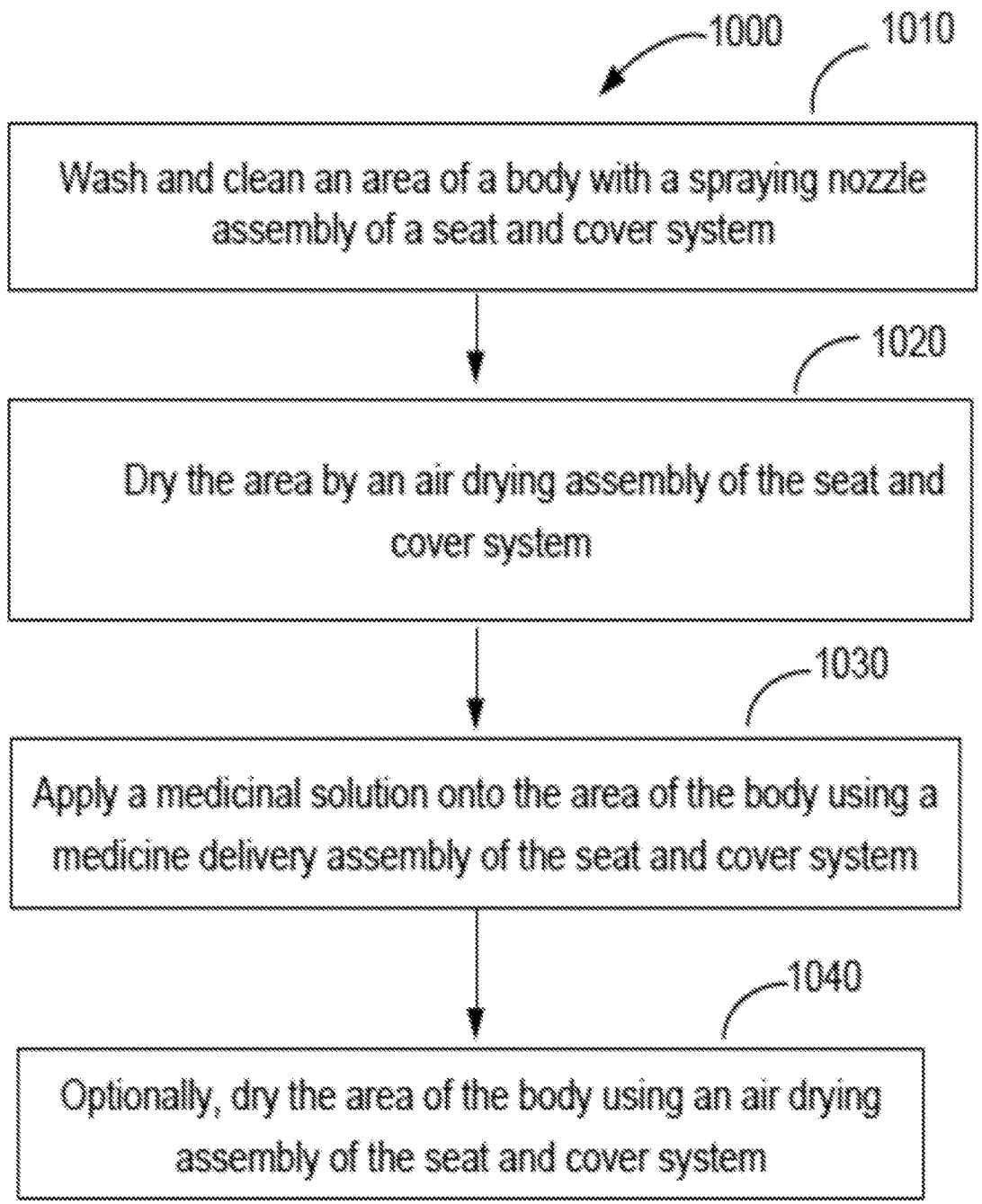
FIG. 17 is a flow chart of a method of using the system of the invention according to embodiments of the invention.

FIG. 17 is a flow chart of a method 1000 of using a seat and cover system of the invention to deliver a solution to a region of a human body. The method 1000 includes washing an area of the region with a spraying nozzle assembly of the seat and cover system at step 1010. In addition, the area of the region with the spraying nozzle assembly of the seat and cover system can be cleaned with a cleaning solution.

Step 1010 may include controlling one or more movements of a spraying nozzle assembly by one or more control units, directing one or more three-dimensional rotational movements of one or more spray nozzle units of the spraying nozzle assembly by communicating one or more control units with one or more first driving motors connected to the one or more spray nozzle units, and directing one or more extending and retracting movements of the one or more spray nozzle units of the spraying nozzle assembly by communicating the one or more control units with one or more second driving motors connected to the one or more spray nozzle units. The step 1010 may also include jetting out water from a first nozzle jet head opening of a first spray nozzle channel within the one or more spray nozzle units, and jetting out the solution from a second nozzle jet head opening of a second spray nozzle channel within the one or more spray nozzle units.

Further, during step 1010, a first spray nozzle channel is adapted to deliver water to the region of the human body for washing the region, and a second spray nozzle channel is adapted to deliver a cleaning solution to the region of the human body for cleaning the region. In another aspect, the second spray nozzle channel is adapted to deliver a medicine-containing solution to the region of the human body for treating the region. In still another aspect, a first spray nozzle channel is connected to a first liquid line to deliver a washing solution to the region of the human body for washing the region, and a second spray nozzle channel is connected to a second liquid line to deliver a cleaning solution to the region of the human body for cleaning the region. In yet another aspect, the first spray nozzle channel is connected to a first liquid line to deliver a washing solution to the region of the human body for washing the region, and the second spray nozzle channel is connected to a second liquid line to deliver a medicine-containing solution to the region of the human body for treating the region.

At step 1020, the area of the body of the user near a drying nozzle assembly of the seat and cover system is dried. The step 1020 may include controlling one or more movements of a drying nozzle assembly by one or more control units, including directing one or more three-dimensional rotational movements of one or more drying nozzle units of the drying nozzle assembly by communicating one or more control units with one or more first driving motors connected to the one or more drying nozzle units, and directing one or more extending and retracting movements of the one or more drying nozzle units of the drying nozzle assembly by communicating the one or more control units with one or more second driving motors connected to the one or more drying nozzle units.

In one embodiment, air from a drying nozzle opening is blown out at a predetermined temperature and a predetermined speed. The step 1020 may also include rotating a nozzle tip portion within the one or more spray nozzle units so that the air is adjusted to be deliver to a desired region of the human body, and adjusting one or more retractable elements within the one or more spray nozzle units by retracting and extending so that the air is adjusted to be deliver to a desired region of the human body. In addition, the step 1020 further includes receiving a user input from the drying nozzle assembly from the one or more control units, and adjusting the one or more extending and retracting movements of the one or more drying nozzle unit based on the user input. Further, the step 1020 further includes receiving a user input from the drying nozzle assembly from the one or more control units; and adjusting the one or more three-dimensional rotational movements of the one or more drying nozzle unit based on the user input.

At step 1030, a medicine-containing solution is applied onto the area using a medicine delivery assembly of the seat and cover system. The step 1030 includes providing one or more medicines to a medicine delivery assembly which is coupled to a toilet seat assembly, and controlling one or more movements of the medicine delivery assembly by one or more control units. In one aspect, controlling the movements of the medicine delivery assembly includes directing one or more extending and retracting movements of a medicine delivery nozzle of the medicine delivery assembly by communicating the one or more control units with one or more first driving motors connected to the medicine delivery nozzle, and directing one or more three-dimensional rotational movements of the medicine delivery nozzle of the medicine delivery assembly by communicating the one or more control units with one or more second motors connected to the medicine delivery nozzle.

At step 1040, optionally, the area of the body is dried again with an air drying assembly of the seat and cover system. Drying the area is performed similar to step 1020; however, the speed and temperature of the air blown to the area of the body may differ, and can be adjusted according to personal preference.

The system provided here present a safer, more hygienic, and more effective alternative method to self-administer perineal medicines than any option currently available. To this extent, the system can present a discreet, "hands-free" alternative to the current options, or couple to other system, such as a bidet toilet seat system, thereby substantially eliminating any discomfort, ineffectiveness, and/or embarrassment a user might otherwise experience.

While the foregoing is directed to embodiments of the present invention, other and further embodiments of the invention may be devised without departing from the basic scope thereof, and the scope thereof is determined by the claims that follow.

The invention claimed is:

1. A toilet seat assembly for delivering medicine, washing, cleaning, and drying a perineal region of a human body, the toilet seat assembly comprising:
   a spraying nozzle assembly disposed at a rearward position in the toilet seat assembly, the spraying nozzle assembly including one or more spray nozzle units, each spray nozzle unit comprising one or more retractable spray nozzle bodies and including a first spray nozzle channel configured to deliver a first liquid and a second spray nozzle channel configured to deliver a second liquid;
   a drying nozzle assembly including one or more drying nozzle units, each drying nozzle unit comprising one or more retractable drying nozzle bodies; and
   a medicine delivery assembly disposed at a forward position in the toilet seat assembly, the medicine delivery assembly including a retractable and extendable medicine delivery nozzle operatively connected to the spraying nozzle assembly, wherein the retractable and extendable medicine delivery nozzle is (i) operatively residing within the toilet seat assembly; (ii) fluidically coupled to a medicine storage element configured to store a medicinal product; (iii) adapted to move in a direction retracting into a front end of a spray nozzle unit; (iv) adapted to move in a direction extending out of the front end of the spray nozzle unit; (v) adapted to move in a vertical direction or a rotational direction about a rotational axis at an angle with a longitudinal axis of the medicine delivery nozzle unit; and (vi) adapted to deliver medicine independently of the spraying nozzle assembly by delivering the medicine without going through the spraying nozzle assembly positioned near a base housing;
   a motor-gear arrangement comprising: one or more motors operatively connected to a first spray nozzle body in the one or more spray nozzle units, a second spray nozzle body in the one or more spray nozzle units, two or more steering gears which contact each other, and the retractable and extendable medicine delivery nozzle;
   wherein the spraying nozzle assembly is configured to deliver at least one liquid product to the region via the one or more spray nozzle units;
   wherein the drying nozzle assembly is configured to deliver air at a predetermined temperature to the region; and
   wherein the medicine delivery assembly is configured to deliver the medicinal product to the region via the retractable and extendable medicine delivery nozzle.

2. The toilet seat assembly of claim 1, wherein:
   the one or more motors are operatively coupled to the spraying nozzle assembly;
   one of the one or more motors is configured to move the one or more spray nozzle units between a retracted position and an extended position.

3. The toilet seat assembly of claim 2, wherein one of the one or more motors is configured to rotate the one or more spray nozzle units about an axis of rotation at an angle with longitudinal axes of the one or more spray nozzle units.

4. The toilet seat assembly of claim 1, wherein the first liquid product comprises one or more of water, a cleaning solution, and a medicine containing solution, and wherein the second liquid product comprises one or more of water, a cleaning solution, and a medicine containing solution.

5. The toilet seat assembly of claim 1, wherein one of the one or more motors is configured to move the retractable medicine delivery nozzle between a retracted position and an extended position.

6. The toilet seat assembly of claim 1, wherein the medicine storage element comprises one or more medicine base units, each medicine base unit including at least one cartridge slot configured to receive a removable medicine storage cartridge containing the medicinal product.

7. The toilet seat assembly of claim 1, wherein the medicine storage assembly further comprises a sensor configured to indicate a status of the medicinal product contained in the medicine storage element.

8. The toilet seat assembly of claim 1 further comprising:
one or more driving motors operatively coupled to the drying nozzle assembly, wherein one of the one or more driving motors is configured to move the one or more drying nozzle units between a retracted position and an extended position, and wherein one of the one or more driving motors is configured to rotate the one or more drying nozzle units about an axis of rotation at an angle with longitudinal axes of the one or more drying nozzles.

9. The toilet seat assembly of claim 1, further comprising:
one or more control units adapted to receive a user input and, based on the user input, cause operation of one or more of the spraying nozzle assembly, the drying nozzle assembly, and the medicine delivery assembly.

10. A method of using a toilet seat assembly including a spraying nozzle assembly disposed at a rearward position in the toilet seat assembly, a drying nozzle assembly, and a medicine delivery assembly, the method comprising:
washing, by a retractable spray nozzle unit of the spraying nozzle assembly, a perineal region of a user with a liquid product, the liquid product comprising one or more of water and a cleaning solution;
delivering air, by a drying nozzle unit of the drying nozzle assembly, to the perineal region at a predetermined temperature; and
applying a medicinal product, by a medicine delivery nozzle of the medicine delivery assembly, to the perineal region, without going through the spraying nozzle assembly positioned near a base housing wherein the medicine delivery nozzle is: (i) operatively residing within the toilet seat assembly, (ii) fluidically coupled to a medicine storage element configured to store a medicinal product, (iii) retractable and extendable, thereby moving in: (a) a direction extending out of the front end of the spray nozzle unit and (b) a vertical direction or a rotational direction about a rotational axis at an angle with a longitudinal axis of the medicine delivery nozzle, via motor-gear arrangement comprising: one or more motors operatively connected to a first spray nozzle body, a second spray nozzle body in the spray nozzle unit and one or more steering gears, and the retractable spray nozzle unit.

11. The toilet seat assembly of claim 1, wherein the first spray nozzle channel is connected to a first liquid reservoir via a first liquid line, and the second spray nozzle channel is connected to a second liquid reservoir via second liquid line.

12. The toilet seat assembly of claim 1, wherein the toilet seat assembly is a bidet seat configured to be installed on a pre-existing toilet bowl.

13. The toilet seat assembly of claim 1, wherein the medicine delivery nozzle is encapsulated within the toilet assembly at the forward position.

14. The toilet seat assembly of claim 2, wherein one of the one or more motors is configured to move the one or more spray nozzle units in a vertical direction.

15. The toilet seat of assembly of claim 6, wherein:
the toilet seat assembly comprises a seat portion configured to accommodate and be sat upon by a user;
the at least one cartridge slot is located at a side of the seat portion.

* * * * *